United States Patent [19]
Becnel et al.

[11] Patent Number: 5,907,069
[45] Date of Patent: May 25, 1999

[54] PRODUCTION OF NABUMETONE OR PRECURSORS THEREOF

[75] Inventors: Brian F. Becnel, Port Allen; Mahmood Sabahi; Kevin J. Theriot, both of Baton Rouge, all of La.

[73] Assignee: Albemarle Corporation, Richmond, Va.

[21] Appl. No.: 09/009,510

[22] Filed: Jan. 20, 1998

Related U.S. Application Data

[62] Division of application No. 08/731,806, Oct. 21, 1996, Pat. No. 5,756,851.

[51] Int. Cl.$^6$ .......................... C07C 39/38; C07C 39/14; C07C 41/00; C07C 47/52
[52] U.S. Cl. .......................... 568/737; 568/735; 568/634; 568/440; 568/328; 568/303
[58] Field of Search ..................... 568/328, 634, 568/737, 303, 440, 735

[56] References Cited

U.S. PATENT DOCUMENTS

| | | | |
|---|---|---|---|
| 2,025,032 | 12/1935 | Arnold et al. | 260/168 |
| 3,880,932 | 4/1975 | Anderson et al. | 260/590 |
| 4,061,779 | 12/1977 | Lake et al. | 424/331 |
| 4,182,912 | 1/1980 | Foley | 568/649 |
| 4,221,741 | 9/1980 | Gaster | 568/314 |
| 4,246,164 | 1/1981 | Felder et al. | 260/501.17 |
| 4,246,193 | 1/1981 | Holton | 260/501.17 |
| 4,247,709 | 1/1981 | Rose et al. | 560/53 |
| 4,270,004 | 5/1981 | Rose et al. | 568/314 |
| 4,299,844 | 11/1981 | Goudie | 424/308 |
| 4,420,639 | 12/1983 | Lake et al. | 568/328 |
| 4,426,392 | 1/1984 | Goudie | 424/308 |
| 4,515,811 | 5/1985 | Holton | 514/554 |
| 4,556,738 | 12/1985 | Kawashima et al. | 564/329 |
| 4,628,123 | 12/1986 | Borsotti | 568/634 |
| 4,697,036 | 9/1987 | Giordano et al. | 562/418 |
| 4,734,507 | 3/1988 | Giordano et al. | 549/450 |
| 4,952,596 | 8/1990 | Della Bella et al. | 514/365 |
| 4,988,416 | 1/1991 | Troupel et al. | 204/59 R |
| 5,093,011 | 3/1992 | Friedman et al. | 210/757 |
| 5,132,466 | 7/1992 | Dales et al. | 568/631 |
| 5,225,603 | 7/1993 | Aslam et al. | 568/328 |
| 5,243,088 | 9/1993 | Jacquot et al. | 568/656 |
| 5,256,829 | 10/1993 | Jacquot | 568/737 |
| 5,426,243 | 6/1995 | Lecouve | 568/737 |

FOREIGN PATENT DOCUMENTS

| | | |
|---|---|---|
| 8201004 | 10/1983 | Brazil . |
| 0179447 | 4/1986 | European Pat. Off. . |
| 0338898 | 7/1992 | European Pat. Off. . |
| 0376516 | 2/1993 | European Pat. Off. . |
| 2647440 | 11/1990 | France . |
| 2338811 | 2/1975 | Germany . |
| 46347 | 12/1974 | Israel . |
| 8700353 | 9/1987 | Netherlands . |
| 8700354 | 9/1987 | Netherlands . |
| 8700355 | 9/1987 | Netherlands . |
| 8700356 | 9/1987 | Netherlands . |
| 8700357 | 9/1987 | Netherlands . |
| 8700358 | 9/1987 | Netherlands . |
| 8700656 | 10/1987 | Netherlands . |
| 8803088 | 7/1989 | Netherlands . |
| 8900721 | 10/1989 | Netherlands . |
| 519548 | 2/1983 | Spain . |
| 536329 | 9/1984 | Spain . |
| 537310 | 11/1984 | Spain . |
| 550601 | 12/1985 | Spain . |

OTHER PUBLICATIONS

Summers et al., "Hydroxamic Acid Inhibitors of 5–Lipoxygenase", J. Med. Chem., 1987, vol. 30, pp. 574–580.

Wong et al., "Synthesis of Novel–centrosymmetric Crystalline Materials for Quadratic Non–linear Optics", J.Chem. Soc., Chem. Commun., 1994, pp. 249–250.

CAPLUS abstract of DE 2338811 (copy of original text enclosed).

WPIDS abstract of DE 2338811 (copy of original text enclosed).

5–Bromo–2,3–benzotropone and its Maleic Anhydride Adduct, Bull. of the Chem. Soc. of Japan, 1971, vol. 44(12) pp. 3480–3481, Ebine, et al.

4–(6–Methoxy–2–naphthyl)butan–2–one and related Analogues, a Novel Structural Class of Antiinflammatory Compounds, J. of Medicinal Chemistry, 1978, vol. 21(12), pp. 1260–1264, Goudie, et al.

(List continued on next page.)

*Primary Examiner*—Jose G. Dees
*Assistant Examiner*—Alton Pryor
*Attorney, Agent, or Firm*—E. E. Spielman, Jr.

[57] ABSTRACT

In producing nabumetone or precursor thereof, use is made of 2-bromo-6-methoxynaphthalene formed by (a) methylating 6-bromo-2-naphthol with methyl bromide or methyl chloride, in a halogen-free liquid solvent comprising at least about 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base; and (b) recovering and purifying 2-bromo-6-methoxynaphthalene so formed. The 6-bromo-2-naphthol in turn is preferably formed by reacting 1,6-dibromo-2-naphthol with hydrogen in a halogen-containing liquid solvent comprising at least about 50% by weight of (A) at least one liquid organic halide solvent in which the halogen content has an atomic number of 35 or less or (B) a mixture of water and at least one such liquid organic halide solvent, and in the presence of catalytic amounts of (i) a tungsten carbide-based catalyst, and (ii) at least one phase transfer catalyst, most preferably while purging HBr from the reaction mixture as it is formed. In this way, the quantities of by-products formed in the overall operation are reduced, the need for use of excess iron and/or dimethyl sulfate as reaction components is avoided, and the overall efficiency of plant operation is improved especially when conducted on a large scale.

43 Claims, No Drawings

OTHER PUBLICATIONS 3,4–Benzotropolone and Related Compounds. VI. Brominated 6–Hydroxy–2,3–benzotropone (or Brominated 3–Hyroxy–4,5–benzotropone). Formation and Reaction, Bull of the Chem. Soc. of Japan, 1968, vol. 41, pp. 2949–2953, Hoshino, et al.

Hard Acid and Soft Nucleophile Systems. 8. Reductive Dehalogenation of o– and p–Halophenols and Their Derivatives, J. Org. Chem., 1984, vol. 49, pp. 3641–3643, Node, et al.

Reversible Bromination. I. Isomerization and Disproportionation of p–Bromophenols, The J. of Org. Chem., 1970, vol. 35(1), pp. 16–19, O'Bara, et al.

X–Philic Reactions, Chem. Rev., 1982, vol. 82(6), pp. 615–624, Zefirov, et al.

Aslam, et al., "Convenient Synthesis of Nabumetone", Synthesis, Nov. 1989, vol. 11, pp. 869–870.

Chatterjea, et al., "Condensation of Mannich Base Salts with Phenols: Orientation of Adducts", Indian Journal of Chem., vol. 11, Mar. 1973, pp. 214–218.

Chen, et al., "Synthesis of Nabumetone by Palladium Catalyzed Coupling", Zhong Guo Yi Yao Gong Ye Za Zhi, vol. 25 (2), 1994, translated pp. 49–50, 57.

Chen, et al., "Novel Synthesis of Nabumetone", Zhong Guo Yi Yao Gong Ye Za Zhi, 1989, vol. 20(4), translated pp. 145–146.

Horeau et al., "No. 287. Setroids Devoid of C Nucleus (III). On a Lactone Corresponding to an Isomer of Bis–Dehydroestrolactone", Soc. Chim., 5th Series, 1959—Reports, translated pp. 1854–1857.

Liu, et al., "Synthesis of Nabumetone", Yi Yao Gong Ye, 1985, vol. 16(4), translated pp. 147–149.

Yin, et al., "Experiments on Preparation of Nabumetone", Zhong Guo Yi Yao Gong Ye Za Zhi, 1990, vol. 21(5), translated pp. 195–196.

Zhang, et al., "Synthesis of a Nonsteroidal Anti–Inflammatory Agent—Nabumetone", Journal of Shenyang College of Pharmacy, vol. 5(4), Oct. 1988, Sum 37, translated pp. 259–263, 267.

PRODUCTION OF NABUMETONE OR PRECURSORS THEREOF

REFERENCE TO RELATED APPLICATION

This is a division of commonly-owned co-pending application Ser. No. 08/731,806, filed Oct. 21, 1996, now U.S. Pat. No. 5,756,851.

TECHNICAL FIELD

This invention relates to processes for the synthesis of nabumetone or precursors thereof, and more particularly to novel environmentally-friendly process technology suitable for producing such materials on a commercial scale.

BACKGROUND

Nabumetone, 4-(6'-methoxy-2'-naphthyl)-butan-2-one, is a well known non-steroidal antiinflammatory agent described for example in U.S. Pat. No. 4,420,639. While various synthesis procedures for its production have been proposed and studied, the most efficacious procedures utilize 2-bromo-6-methoxynaphthalene (also known as 6-bromo-2-methoxynaphthalene) as a key starting material or chemical intermediate. This product is usually formed by hydrodebromination of 1,6-dibromo-2-naphthol by use of iron powder in an aqueous acid medium to form 6-bromo-2-naphthol, followed by treatment with dimethyl sulfate and sodium hydroxide to effect methylation of the hydroxyl group. Unfortunately this process approach suffers from need for long cycle times, formation of large amounts of co-products from both reaction steps, need for use of stoichiometric excesses of dimethyl sulfate and iron, and lower than desired plant throughput. Another method of producing 2-bromo-6-methoxynaphthalene is suggested in U.S. Pat. No. 5,256,829 where hydrodebromination of 1,6-dibromo-2-naphthol to 6-bromo-2-naphthol is effected by use of hydrogen and a tungsten carbide-based catalyst in an acidic organic solvent, and where the reagents taught for use in the methylation step are methyl sulfate or methanol. Despite the intensity and scope of prior investigations of such process steps, a need exists for process technology capable of reducing the quantities of by-product wastes formed in the operation, of avoiding the need for use of excess iron and/or dimethyl sulfate as reaction components, and of improving the overall efficiency of plant operation when conducted on a large scale.

This invention is deemed to fulfill this need in an efficient and effective manner.

SUMMARY OF THE INVENTION

In one of its embodiments this invention provides improvements in a process for production of nabumetone or precursor thereof from 2-bromo-6-methoxynaphthalene. The improvements involve using in the process a 2-bromo-6-methoxynaphthalene product formed by a process comprising:

a) methylating 6-bromo-2-naphthol with methyl bromide or, preferably, methyl chloride in a halogen-free liquid solvent comprising at least 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base such that 2-bromo-6-methoxynaphthalene is formed; and b) recovering and purifying 2-bromo-6-methoxynaphthalene so formed.

Another embodiment is the use in a process for producing nabumetone or precursor thereof of 2-bromo-6-methoxynaphthalene formed by a process which comprises:

A) reacting 1,6-dibromo-2-naphthol with hydrogen or a precursor compound that generates nascent hydrogen in the medium of the reaction, in a halogen-containing liquid solvent comprising at least about 50% by weight of (a) at least one liquid organic halide solvent in which the halogen content has an atomic number of 35 or less or (b) a mixture of water and at least one such liquid organic halide solvent, and in the presence of catalytically effective amounts of (i) a tungsten carbide-based catalyst, and (ii) at least one phase transfer catalyst, such that 6-bromo-2-naphthol is formed;

B) separating 6-bromo-2-naphthol so formed from said organic halide solvent so that the 6-bromo-2-naphthol is at least substantially completely free from any halogen-containing impurity content;

C) methylating 6-bromo-2-naphthol from B) with methyl bromide or methyl chloride, or both, in a halogen-free liquid solvent comprising at least about 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base such that 2-bromo-6-methoxynaphthalene is formed; and D) recovering and purifying 2-bromo-6-methoxynaphthalene so formed.

Other embodiments of this invention make it possible not only to produce nabumetone and/or one or more precursors of nabumetone such as, for example, 6-methoxy-2-naphthaldehyde, 4-(6'-methoxy-2'-naphthyl)-2-buten-3-one (also sometimes named in the prior art as 4-(6'-methoxy-2'-naphthyl)-3-buten-2-one), 4-(6'-methoxy-2'-naphthyl)-2-buten-3-ol (also sometimes named in the prior art as 4-(6'-methoxy-2'-naphthyl)-3-buten-2-ol), 2-methoxy-6-vinylnaphthalene, 6-methoxynaphthylmagnesium bromide, and 1-(6'-methoxy-2-naphthyl)ethane, etc., but also to produce 6-bromo-2-naphthol and 2-bromo-6-methoxynaphthalene on a large scale by highly efficient, environmentally-friendly processes. Indeed, the process technology of this invention is capable of producing these materials of a purity suitable for use in the production of naproxen as well as for use in nabumetone synthesis.

Thus a further embodiment is producing 2-bromo-6-methoxynaphthalene by a process which comprises methylating 6-bromo-2-naphthol with methyl bromide or, preferably, methyl chloride in a halogen-free liquid solvent comprising at least 40% by weight of one or more compounds of the formula RZ where R is a hydrogen atom or an alkyl group, and 7 is a hydroxyl group or a cyanide group with the proviso that if Z is a cyanide group, R is an alkyl group, and in the presence of at least one strong base such that 2-bromo-6-methoxynaphthalene is formed.

Still another embodiment is a process of producing 6-bromo-2-naphthol that comprises reacting 1,6-dibromo-2-naphthol with hydrogen or a precursor compound that generates nascent hydrogen in the medium of the reaction, in a halogen-containing liquid solvent comprising at least about 50% by weight of (a) at least one liquid organic halide solvent in which the halogen content has an atomic number of 35 or less or (b) a mixture of water and at least one such liquid organic halide solvent, and in the presence of catalytically effective amounts of (i) a tungsten carbide-based catalyst, and (ii) at least one phase transfer catalyst, and in the presence at the start of the reaction of a small, reaction-initiating amount of an acid, preferably a carboxylic acid or better yet, a mineral acid or anhydride, most preferably hydrobromic acid or hydrogen bromide, such that 6-bromo-2-naphthol is formed, and substantially continuously purging hydrogen bromide from the reaction mixture substantially as soon as it is formed.

These and other embodiments and features of this invention will be still further apparent from the ensuing description and appended claims.

FURTHER DESCRIPTION OF THE INVENTION

Methylation of 6-bromo-2-naphthol

As noted above, this invention involves, inter alia, the process of methylating 6-bromo-2-naphthol with methyl bromide or, preferably, methyl chloride to produce 2-bromo-6-methoxynaphthalene. Use of these methylating reagents, especially methyl chloride, instead of dimethyl sulfate is of considerable advantage in that large excesses of dimethyl sulfate (60–70%) are normally required for adequate yields of the desired product. Furthermore, the reaction with dimethyl sulfate utilizes only one of the two methyl groups and consequently leads to the generation of an aqueous co-product stream containing sodium methyl sulfate. The safe and environmentally satisfactory disposal of such a stream is not without considerable difficulty and expense.

Pursuant to this invention, the methylation with methyl bromide or methyl chloride is performed in a halogen-free liquid solvent comprising at least 40% by weight (preferably in the range of about 40 to about 70% by weight) of one or more compounds of the formula RZ where R is a hydrogen atom or an alkyl group, and Z is a hydroxyl group or a cyanide group (with the proviso that if Z is a cyanide group, R is an alkyl group), and in the presence of at least one strong base. These solvents thus include water, alcohols, nitrites, and mixtures thereof. Of these materials water, one or more alcohols, and mixtures, especially single phase mixtures of water and one or more alcohols are preferred from the cost effectiveness standpoint. Suitable nitrites include acetonitrile, propionitrile, butyronitrile, $\alpha$-methylbutyronitrile, benzonitrile, and similar liquid cyclic and acyclic nitrites, including mixtures of two or more such materials. Aliphatic and alicyclic alcohols, including diols, suitable for use include methanol, ethanol, 1-propanol, 2-propanol, 1-butanol, 2-methyl-1-propanol, 1-pentanol, 1-hexanol, cyclopentanol, 2-ethoxyethanol, ethylene glycol, and analogous compounds, including mixtures of two or more such alcohols. Of these solvents, liquid lower alkanols having 2 to 4 carbon atoms, especially 2-propanol, and single phase mixtures of lower alkanols with water, especially mixtures of 2-propanol and water, are preferred. More preferred are solvents composed of at least 98 weight percent or more of a liquid alcohol, of which substantially pure 2-propanol, or substantially pure 2-propanol containing up to about 2 wt % water, are especially preferred.

It is of great importance to ensure that the reaction mixture used in the methylation process is free of organic halogen-containing impurities as such materials, if present, can react with the 6-bromo-2-naphthol and/or 2-bromo-6-methoxynaphthalene to produce undesirable by-products.

The methylation reaction is performed in the presence of a strong base, i.e., in a strongly basic liquid reaction medium. For this purpose the most cost effective bases comprise inorganic bases such as the oxides and hydroxides of sodium and potassium. Use of such materials with water or suitable alcohols or combinations of one or more suitable alcohols with water serve as examples of such media. Suitable organic bases that can be used include sodium or potassium alkoxides (e.g., sodium methoxide, potassium methoxide, sodium ethoxide, potassium ethoxide, sodium isopropoxide, potassium isopropoxide, etc.), alkaline amide salts (e.g., sodium amide, potassium amide, sodium isopropyl amide, potassium ethylamide, etc.), and similar materials. As is well known to chemists, upon addition to water or alcohols certain bases such as the hydroxides lose their identity while in solution by virtue of ionization. Likewise the oxides undergo transformations so that ionization occurs and upon drying of the solution the hydroxide remains. As will be made even clearer hereinafter, this invention is not limited in any way by preliminary changes or transformations which occur as a natural consequence of bringing two or more materials together. For example, addition of sodium hydroxide to an alcohol such as 1-propanol is generally regarded as resulting in the formation of an alkoxide, in this case, sodium propoxide. But for the purposes of this invention the actual composition of the material while in solution is immaterial.

The methylation process of this invention is usually performed at temperatures in the range of about 25 and about 140° C., and preferably in the range of about 50 and about 100° C. The mol ratio of methyl bromide or methyl chloride to 6-bromo-2-naphthol will usually be in the range of about 1.0 to about 1.2 mols of the methyl halide per mol of the 6-bromo-2-naphthol. The reaction solution will generally contain from about 1.0 to about 1.1 mol percent of added strong base per mole of 6-bromo-2-naphthol charged. Reaction periods in the range of about 1 hour to about 6 hours will usually suffice. The reaction is conveniently conducted in a closed reaction vessel under autogenous pressure, but can be performed under various pressure conditions ranging from atmospheric pressures to superatmospheric pressures (e.g., 100–200 psig).

To date, experience has shown that the use of methyl chloride is much preferred over use of methyl bromide as the latter, while operable, has yielded products containing one or two major impurities in the range of about 10–15 wt %. Based on these results, methyl iodide should also be an operable methylating agent for use in the process, and is expected to lead to the desired product in high yields.

The following examples illustrate preferred procedures for conducting the methylation reaction in accordance with this invention. In the examples the following abbreviations are used: 6-BN is 6-bromo-2-naphthol; BMN is 2-bromo-6-methoxynaphthalene; MBMN is 2-bromo-6-methoxy-armethylnaphthalene, a by-product impurity; DBMN is dibromo-methoxynaphthalene, an impurity; TBMN is tribromo-methoxynaphthalene, another impurity; MN is methoxynaphthalene; TBAB is tetrabutylammonium bromide; and EDC is ethylene dichloride.

EXAMPLE 1

Methylation with Methyl Chloride in Water. A 300 mL autoclave was charged with 6-BN (0.2 mol, 44.6 g), sodium hydroxide (0.25 mol, 20 g of 50%), water (140 mL) and then purged with nitrogen and sealed. Methyl chloride (0.3 mol, 15.8 g) was added and the reaction mixture was heated at 125° C. for five hours. The pressure reached a maximum of 150 psi. At the end, the reactor was cooled to room temperature and excess methyl chloride was released into scrubbers. Solid BMN was filtered from the acidic aqueous phase. Analysis of the solid showed 87% BMN, 8% unreacted 6-BN, 4% MBMN, and 1% methoxynaphthalene.

EXAMPLE 2

Methylation with Methyl Chloride in Isopropyl Alcohol. Sodium hydroxide (0.22 mol, 8.8 g; 17.6 g of 50%) was added to isopropyl alcohol (120 g; 150 mL). The stirred mixture was degassed with nitrogen and then 6-BN (0.2 mol, 44.6 g) was added. The resulting solution was purged with nitrogen and placed in an autoclave and charged with methyl chloride (0.47 mol, 24 g) which dissolved in the solution very rapidly at room temperature. The mixture was heated to 66° C. and achieved a maximum pressure of 80 psi. The pressure stabilized after about four hours. The mixture was then heated at 80° C. for another two hours and then cooled. Excess methyl chloride was released into traps and the autoclave was opened. The yellow solid mass was filtered and washed with water. GC analysis of the crude showed only BMN. The product was dried under vacuum (42.6 g, 90%) and analyzed by GC and GC-mass spec.: 99.4 wt % BMN, 0.06% MN, 0.04% 6-BN, 0.2% DBMN.

EXAMPLE 3

Hydrodebromination of DBN. A solution of DBN (196 g, 0.65 mol) in EDC (348 g) is charged in a one-liter Hastalloy B autoclave. Tungsten carbide (43.7 g, 20 wt %) and tetrabutylammoniu bromide (1.1 g, 0.5 wt %) are added and the reactor is sealed. The reactor is purged with hydrogen (50 psig) and vented three times and then pressured with hydrogen and heated to 110° C. A constant purge of hydrogen is maintained at such a rate that the pressure remains in the 100–110 psig range. Analysis of a product mixture formed in this general manner showed 92.3% 6-BN, 0.8% DBN, and 1.9% 2-naphthol. The reactor is cooled to room temperature, vented to scrubbers, and the WC catalyst is permitted to settle. The EDC solution is removed through the dip tube. A portion of the EDC solution is concentrated by distillation. When the pot temperature reaches around 100° C., water (50 mL) is added to azeotropically remove the remainder of EDC without raising the temperature of the crude 6-BN. When all of the EDC is removed (judged by the overhead temperature) the crude is analyzed. In an operation conducted in this general manner the crude product was found to contain 6-BN (55 g, 250 mmol) as the major component.

Methylation of 6-BN with Methyl Chloride. Isopropyl alcohol (150 mL) and sodium hydroxide (11 g, 280 mmol; 22 g of 50% solution) were added to such crude product and the mixture was sealed in an autoclave. Methyl chloride (18 g, 350 mmol) was introduced at room temperature and the autoclave was heated to 76° C. After four hours the reaction was stopped and the excess methyl chloride was removed. A solid mass was recovered with little liquid phase. The slurry had a pH of 12–13, and was acidified by dilute hydrochloric acid. Isopropyl alcohol was removed by simple distillation and water (100 mL) was added to the residue. The mixture was heated to about 100° C. (which melted the crude) with fast stirring. The mixture was settled and the aqueous layer was separated from the molten BMN. BMN was distilled under reduced pressure (1 mmHg, 160–165° C.). The white solid distillate was crystallized from isopropyl alcohol (200 mL). The white solid (42 g, 72%) was analyzed by GC: BMN 97.1 wt %, MBMN 0.2%, MN 0.1%, DBMN 0.6%, and TBMN 2.0%.

EXAMPLE 4

Methylation with Methyl Chloride in Acetonitrile. To a solution of 6-BN (15.6 g, 70 mmol) in acetonitrile (50 mL) was added potassium hydroxide pellets (4.5 g, 80 mmol) and tetrabutylammonium bromide (0.5 g). The resulting mixture was transferred to an autoclave and charged with methyl chloride (6 g, 120 mmol) and heated to 70° C. After three hours it was cooled to room temperature. Analysis of the crude reaction mixture showed only BMN.

EXAMPLE 5

Methylation with Methyl Chloride in Acetonitrile. The above reaction was repeated with 6-BN from a regioselective hydrodebromination reaction conducted as described in detail hereinafter, and with sodium hydroxide pellets. The crude product contained: 98.4% BMN, 1.0% 6-BN, 0.4% DBMN, 0.1% MN.

EXAMPLE 6

Methylation with Methyl Chloride in Acetonitrile. The above reaction was repeated with 50% sodium hydroxide and 6-BN, formed by a regioselective hydrodcbromination reaction. Analysis of the crude showed: 96.8% BMN, 0.4% MN, 1.4% 6-BN, 0.6% DBMN, others 0.8%.

EXAMPLE 7

Bromination of 2-Naphthol. 2-Naphthol (144.8 g, 1.00 mol), EDC (537 g), and water (162 g) were charged to a 2-L reactor equipped with a reflux condenser, mechanical stirrer and peristaltic pump addition system. The reactor was heated to about 55° C. until most of the β-naphthol was dissolved. Bromine (336.9 g, 2.11 mol) was then added (sub-surface) via the pump at such a rate so as to maintain the reaction temperature at 60° C. After the bromine addition the reaction temperature was maintained at 60° C. for 1.5 h. The reaction was then cooled slightly and the lower phase (aq. HBr) siphoned off. The remaining EDC solution (841 g) was transferred out of the reactor and analyzed by GC which showed 0.4% 2-naphthol, 92.6% DBN, and 4.9% of other isomers.

Hydrodebromination of DBN. A solution of DBN (271 g, 0.9 mol) in EDC (551 g), obtained from the bromination reaction, was charged in a 1000 mL Hastalloy B autoclave. Tungsten carbide (82 g, 30 wt %) and tetrabutylamrnmonium bromide (0.2 g, 0.1 wt %) were added and the reactor was sealed. The reactor was purged with hydrogen (50 psig) and vented three times and then pressured with hydrogen and heated to 90° C. A constant purge of hydrogen was maintained in such a rate that the pressure remained in the 120–125 psig range. Analysis of the reaction mixture after 5.5 hours showed 90% 6-BN, 2% DBN, and 2% 2-naphthol. The reactor was cooled to room temperature, vented to scrubbers, and the catalyst was permitted to settle. The EDC solution (747 g) was removed through the dip tube.

Methylation of 6-BN with MeCl. The EDC solution was transferred to a 1.4-liter (three pints) Chemco glass reactor with stainless steel head. It was first neutralized with dilute acid and then concentrated by distillation. Water (50 mL) was added to azeotropically remove traces of EDC left in the residue. Isopropyl alcohol (242 g) and sodium hydroxide (44 g, 1.1 mol; 88 g of 50% solution) were charged in the reactor. The reactor was sealed, purged with nitrogen, and heated to 70° C. Methyl chloride (66 g, 1.3 mol) was charged over a period of one hour (40–50 psig). After stirring at 80° C. for another hour, isopropyl alcohol was removed by distillation. The residue was heated to melted condition (90–95° C.) and then it was washed with water (400 g). Water was removed and the residue was distilled under vacuum (1 mmHg). After removing small amounts of volatile materials, BMN was distilled at 160–165° C. as a white solid (169 g). Isopropyl alcohol (490 g) was added and the solution was heated to reflux and then slowly cooled down to about 10° C. Solid BMN was removed and washed with cold (0° C.) isopropyl alcohol (180 g) and then dried under vacuum at 70–75° C. Analysis of the white crystalline product showed 99.7 wt % BMN.

As illustrated in Example 7, upon completion of the methylation reaction, the 2-bromo-6-methoxynaphthalene is recovered and purified. While several different procedures may be envisioned and utilized for accomplishing this, it is important to ensure that the product is of sufficient purity to meet the stringent requirements for use in the synthesis of nabumetone. In accordance with preferred embodiments of this invention two different, but related, procedures have been developed for accomplishing the recovery and purification of 2-bromo-6-methoxynaphthalene when the base used in the methylation reaction is an alkali metal base such as sodium hydroxide or potassium hydroxide. In one such embodiment, the separation and recovery is effected by a procedure which comprises in essence the following three-steps:

1) distilling off the solvent from the methylation reaction product mixture to leave a hot molten residue;
2) washing the residue, while molten, with water to remove alkali metal halide by-product and water-soluble impurities, if any, from the 2-bromo-6-methoxynaphthalene-containing residue; and
3) crystallizing the 2-bromo-6-methoxynaphthalene from a suitable liquid medium. As the crystallization medium for this procedure, use can be made of liquid alcohols, ethers, ketones, nitriles, hydrocarbons, halogenated hydrocarbons, carboxylic acids, and the like. Of such materials, liquid lower alkanols ($C_{1-4}$), especially 2-propanol, are preferred. Mixed solvent systems can also be used, if desired.

The other procedure of this invention for recovering and purifying the 2-bromo-6-methoxynaphthalene comprises in essence four steps, as follows:

1) distilling off solvent from the methylation reaction product mixture to leave a hot molten residue;
2) washing the residue, while molten, with water to remove alkali metal halide by-product and water-soluble impurities, if any, from the residue;
3) distilling 2-bromo-6-methoxynaphthalene from the washed residue; and
4) crystallizing the 2-bromo-6-methoxynaphthalene from a liquid medium.

Here again, the liquid lower alkanols, especially 2-propanol, are preferred for use as the crystallization medium of this procedure. flowever, as above, use can also be made of liquid ethers, ketones, nitriles, hydrocarbons, halogenated hydrocarbons, carboxylic acids, and the like, including mixed solvent systems.

Production of 6-bromo-2-naphthol

Another embodiment of this invention is an efficacious process for the production of 6-bromo-2-naphthol of a purity and composition such that it is eminently suited and especially adapted for use in the above methylation process of this invention. More particularly, this process comprises reacting 1,6-dibromo-2-naphthol with hydrogen or a precursor compound that generates nascent hydrogen in the medium of the reaction. This reaction is performed in a halogen-containing liquid solvent comprising at least 50% by weight of (a) at least one organic halide solvent or (b) a mixture of water and at least one organic halide solvent, such as, for example, a polychloroalkane. In addition, the reaction is performed in the presence of catalytically effective amounts of (i) a tungsten carbide-based catalyst, and (ii) at least one phase transfer catalyst. The 6-bromo-2-naphthol formed in the reaction is separated from (and freed of) the organic halide solvent so that the 6-bromo-2-naphthol is at least substantially completely free from any halogen-containing impurity content. It will be noted that this is a controlled or selective hydrodebromination reaction wherein one of two bromine atoms of the reactant is removed in preference to the other, and the one that remains is in the desired position. Thus the reaction is in fact a regiospecific or regioselective hydrodebromination reaction. These and terms of similar import may be employed hereinafter to refer to this particular reaction.

The liquid organic halides used as solvent media for the hydrodebromination reaction are liquids composed of carbon and halogen atoms, and in most cases hydrogen atoms as well. The halogen content of such solvents is one or more fluorine, chlorine and/or bromine atoms (i.e., halogen of atomic number 35 or less). Thus the solvent medium for the hydrodebromination reaction can be one or more perhalocarbons or one or more halohydrocarbons or a mixture of one or more perhalocarbons or one or more halohydrocarbons, in all cases where the halogen atom content has an atomic number of 35 or less. These solvents can have one or more halogen atoms in the molecule, and when two or more halogen atoms are present in the molecule, they can be the same or different halogen atoms (i.e., they can be fluorine and chlorine atoms, chlorine and bromine atoms, fluorine and bromine atoms, or fluorine, chlorine and bromine atoms). Preferred solvents for this reaction are the halogen-containing saturated aliphatic compounds, halogen-containing saturated cycloaliphatic compounds and halogen-containing aromatic compounds, and ofthese the chloroalkanes are preferred. Most preferred are polychloroalkanes, especially ethylene dichloride. These solvents may be used in combination with water as a mixed phase reaction medium. Preferably, however, the halocarbon or halohydrocarbon solvent is either anhydrous or it contains small amounts of water and in this latter case, the amount of water is preferably small enough such that the solvent remains visually clear and thus does not possess a visually readily-observable separate liquid phase. The foregoing solvents are desirable media in which to perform this regiospecific or regioselective hydrodebromination reaction. Likewise, the conjoint use of tungsten carbide and phase transfer catalyst in conjunction with such reaction media have afforded both high selectivity and shortened reaction periods. It will be recalled, however, that if the 6-bromo-2-naphthol used in the methylation process is contaminated with organic halogen-containing impurities, the resultant methylation product will, in all likelihood, suffer from the presence of one or more by-products from the interaction of the organic halogen-containing impurities with the 6-bromo-2-naphthol and/or the 2-bromo-6-methoxynaphthalene under the conditions of the methylation reaction. Thus another feature of this process for producing 6-bromo-2-naphthol is the preferred methods by which the 6-bromo-2-naphthol formed in the reaction is separated from (and freed of) the halocarbon and/or halohydrocarbon utilized as the reaction medium or together with water in the reaction medium.

A few examples of halocarbons and halohydrocarbons that can serve as a reaction medium for the regiospecific hydrodebromination reaction include hexafluorobenzene, octafluorotoluene, perfluorodecalin, carbon tetrachloride, chloroform, ethylene dibromide, 1,1-dibromoethane, bromobenzene, chlorobenzene, fluorobenzene, 1-bromo-3-chlorobenzene, 1-chloro-4-fluorobenzene, o-bromotoluene, m-bromotoluene, o-chlorotoluene, m-chlorotoluene, p-chlorotoluene, o-fluorotoluene, m-fluorotoluene, p-fluorotoluene, α-chloro-α,α-difluorotoluenc, 1,1,1,2-tetrachloro-2,2-difluoroethane, 1,1,2,2-tetrachloro-1,2-difluoroethane, 1,1,2-tribromoethane, bromocyclohexane, chlorocyclohexane, trichloroethylene, perchloroethylene, and like compounds.

Polychloroalkanes suitable for use as reaction media for the conversion of 1,6-dibromo-2-naphthol to 6-dibromo-2-naphthol include ethylene dichloride (1,2-dichloroethane), 1,1-dichloropropane, 1,2-dichloropropane, 1,3-dichloropropane, 1,1,1-trichloroethane, 1,1,2-trichloroethane, 1,1,2,2-tetrachloroethane, and dichloromethane. Of these, ethylene dichloride is most preferred.

When water is present in the organic halide solvent, it is desirable to avoid an amount of water that will deactivate the catalyst. Thus the amount of water used is usually less than 10% by weight of the total weight of water plus halocarbon and/or halohydrocarbon solvent. A particularly preferred reaction medium is a visually clear mixture composed of ethylene dichloride and water in which the amount of water is below or up to, but not in excess of, the saturation point when the mixture is at 25 to 30° C. The reaction medium should be essentially free of iron or other dissolved metals that would interfere with the reaction.

The tungsten carbide catalysts used in this reaction are catalysts based on tungsten carbide. The use of such catalysts per se in the hydrodebromination of 1,6-dibromo-2-naphthol with hydrogen to form 6-dibromo-2-naphthol has been reported heretofore, in U.S. Pat. No. 5,256,829 to R. Jacquot. According to the patent, the tungsten carbide catalysts may also comprise, in addition to the tungsten carbide, one or more other metal monocarbides, for example the carbides of molybdenum, vanadium, niobium, tantalum, titanium, iron and chromium. When present, the amount of these other metal carbides is indicated to preferably be in the range of about 0.01% to about 50% by weight with respect to the total amount of all carbides present. According to the patent, the catalyst can be based either on use of bulk tungsten carbide, or on use of supported tungsten carbide, in either case with or without the co-presence of one or more carbides of other metals. Oxides, such as silica, alumina and titanium dioxide, or charcoal, are said to be useful as supports. The patent also refers to use of a monolithic substrate (honeycomb or otherwise) of tungsten carbide or of a monolithic substrate coated with a layer of tungsten carbide, and of finely divided product and made of, or coated with, tungsten carbide. Use of products made by shaping pulverulent materials (powders) such as beads, pellets, spheres, granules, extrudates, agglomerates and others, with a circular, oval, trilobate or multilobate, solid or hollow cross-section is also referred to in the patent. The patent further indicates that tungsten carbide can be used whose specific surface area (BET) ranges from 0.01 to several hundreds of m²/g and, in particular, from 1 to 300 or 400 m²/g.

Most preferably, the tungsten carbide catalyst used in the practice of this invention is in the form of essentially pure tungsten carbide itself in a very fine powdery state, e.g., with an average particle size of about 0.9 micron and containing particles as small as 0.1 micron. Such material has been found to be highly effective when utilized in accordance with the co-catalyzed selective hydrodebromination process of this invention.

Amounts of tungsten carbide-based catalyst are typically in the range of about 5 to about 50 wt % of WC based on the weight of 1,6-dibromo-2-naphthol initially present in the reaction mixture. Preferred amounts of the above preferred finely-divided tungsten carbide are in the range of about 10 to about 30 wt % of WC based on the weight of 1,6-dibromo-2-naphthol initially present.

In the regiospecific hydrodebromination process of this invention, a co-catalyst is employed, namely, at least one phase transfer catalyst. For this purpose use can be made of various types of phase transfer catalysts such as crown ethers, crypt compounds, quaternary phosphonium complexes, and quaternary ammonium complexes. Of these, the quaternary ammonium complexes are most preferred.

Suitable quaternary ammonium complexes include compounds depicted by the formula:

$$R^1R^2R^3R^4N^{\oplus}X^{\ominus}$$

where $R^1$, $R^2$, $R^3$ and $R^4$ are, independently, hydrocarbyl groups (e.g., alkyl, cycloalkyl, aryl, aralkyl, alkenyl, alkoxylated alkylene polyamine groups, alkoxylated hydroxyhydrocarbyl groups, and/or heterocyclic groups in which the heteroatom or atoms are nitrogen atoms), and X is an anion such as a halide ion, a hydroxyl anion, a monoalkylsulfate anion, a sulfonate anion, a hydrogen sulfate anion, or the like. Examples of such compounds include:

tetrabutylammonium bromide
tetrahexylammonium bromide
trimethyldodecylammonium chloride;
trimethyldodecylammonium bromide;
trimethyltetradecylammonium chloride;
trimethyltetradecylammonium bromide;
trimethylhexadecylammonium chloride;
trimethylhexadecylammonium bromide;
trimethyloctadecylammonium chloride;
trimethyloctadecylammonium bromide;
dimethylalkylbenzylammonium chloride; where the alkyl groups are one or more of the following: n-$C_{12}H_{25}$; n-$C_{14}H_{29}$; n-$C_{16}H_{33}$; n-$C_{18}H_{37}$;
methylbis(2-hydroxyethyl)octadecylammonium chloride;
methylpolyoxyethylene (15) octadecylammonium chloride;
n-dodecyl (61%), n-tetradecyl (23%) dimethylbenzylammonium chloride;
n-tetradecyl (60%), n-hexadecyl (30%) dimethylbenzylammonium chloride;
n-dodecyl (40%), n-tetradecyl (50%) dimethylbenzylammonium chloride;
n-dodecyl (61%), n-tetradecyl (23%) dimethylbenzylammonium chloride;
n-octadecyldimethylbenzylammonium chloride;
42% solution of mixed n-tetradecyl (40%) and n-hexadecyl (60%) dimethylbenzylammonium chlorides;
8% solution of dialkylmethylbenzylammonium chloride;
n-dodecyl (35%), tetradecyl (5%), hexadecyl (60%) dimethylbenzylammonium chloride;
n-dodecyl (20%), tetradecyl (50%), hexadecyl (30%) dimethylbenzylammonium bromide;
methyl sulfate quaternary of ethoxylated tallow diethylenetriamine condensate;
methyl sulfate quaternary of propoxylated tallow diethylenetriamine condensate; and
1-(tallow amidoethylene)-2-nor(tallow alkyl)-2-imidazolinium, methyl sulfate quaternary.

Methods of preparation for the quaternary ammonium compounds useful in carrying out the process of this invention are numerous and vary depending on the structure of the final compound. Typical reactions are, for example, reaction of a suitable tertiary amine with an alkylating agent, which can be an alkyl ester or alkyl halide. Such reactions are summarized in Kirk-Othmer, *Encyclopedia of Chemical Technology*, Third Edition, Volume 19.

The quaternary ammonium complex is used in a co-catalytically effective amount, typically in the range of about 0.01 to about 10 wt %, and preferably in the range of about 0.1 to about 1 wt %, of the 1,6-dibromo-2-naphthol initially present.

Quaternary phosphonium complexes which may be employed include compounds depicted by the formula:

$$R^5R^6R^7R^8P^{\oplus}X^{\ominus}$$

where $R^5$, $R^6$, $R^7$ and $R^8$ are, independently, substantially straight chain hydrocarbyl groups (e.g., alkyl, alkenyl, alkoxyalkyl, poly(alkoxy)alkyl, etc., groups which are either non-branched or if branched, have branching in remote positions that do not provide steric hindrance), and X is an anion such as a halide ion. Methods for the preparation of such complexes include reaction of phosphine with sterically unhindered alkyl halides. Examples of such compounds include: tetrabutylphosphonium bromide, hexadecytributylphosphonium chloride, methyltriphenylphosphonium iodide, 2-hydroxyethyltriphenylphosphonium bromide, tetrabutylphosphonium chloride, tetraphenylphosphonium chloride, tetraphenylphosphonium bromide, tetrabutylphosphonium iodide, methyltrioctylphosphonium bromide, and analogous compounds.

Co-catalytically effective amounts of quaternary phosphonium complex used will typically fall in the range of about 0.01 to about 10 wt %, and preferably in the range of about 0.1 to about 1 wt %, of the 1,6-dibromo-2-naphthol initially present.

For descriptions of crown ethers such as 18-crown-6 and crypt compounds such as crypt-222 which may be used in the process, one may refer, for example to such references as U.S. Pat. No. 3,687,978; J. J. Christensen, et al., *Chem. Rev.*, 1974, 74, 351; J. S. Bradshaw, et al., *Heterocycl. Chem.*, 1974, 11, 649; C. J. Pedersen, et al., *Angew. Chem. Int. Ed. Engl.*, 1972, 11, 16; the Technical Bulletin of PCR Incorporated entitled KRYPTOFIX; and *J. Org. Chem.*, 1977, Vol 42, No. 10, 2A. The crown ether or crypt compound is used in a catalytically effective amount, which typically is in the range of about 0.01 to about 0.1 mol per mol of 1,6-dibromo-2-naphthol initially present in the reaction mixture. To initiate the catalyzed regiospecific hydrodebromination reaction, the reaction system should contain a small catalytically effective amount of an acidic substance, most preferably hydrogen bromide. This is typically an amount within the range of about 1 to about 10 wt % of the total weight of the reaction system that ensures that the reaction is initiated and proceeds at a satisfactory rate without at the same resulting in the formation of appreciable quantities of 2-naphthol through overhydrodebromination. The optimum amount in any case should be determined by performing a few pilot tests, as the amount appears to depend upon a number of factors which can vary from case to case and which have defied repeated attempts of identification and quantification, such as the reaction and reaction conditions used to form the 1,6-dibromo-2-naphthol, the purity of the initial 1,6-dibromo-2-naphthol, the amount and makeup of the impurities in the initial 1,6-dibromo-2-naphthol, the materials of construction to which the 1,6-dibromo-2-naphthol was exposed during its formation and before its use, the duration of such exposure, and perhaps other factors.

Experimental studies conducted to date indicate that the tungsten carbide catalyst undergoes little if any change during the course of a number of successive runs. Nevertheless it is entirely possible that during the reaction the tungsten carbide catalyst may enter into transitory changes such as coordinating with or otherwise accepting hydrogen atoms on its surface, and/or forming some form of transitory complex with the phase transfer catalyst. In short, it is not known exactly how (i.e., the mechanism by which) either catalyst component actually functions during the reaction nor the actual state or composition of the catalyst components when functioning in the reaction mixture. Therefore, as regards catalyst composition, the co-catalyst materials are identified herein as to their respective compositions prior to being combined with any other substance being used in the process. After addition to, and/or mixing with, one or more other components used in the process and/or during the course of the process itself, either or both co-catalysts may change in its respective composition, and if so, the resultant changed material—whatever its makeup and however many changes it may undergo—may be in whole or in part responsible for the functioning of the catalyst.

As indicated above, it is highly desirable, if not highly important, to ensure that the liquid phase of the controlled hydrodebromination reaction contains an acidic catalyst most preferably hydrogen bromide during at least substantially the entire reaction period of such hydrodebromination reaction. Accordingly, unless absolutely pure 1,6-dibromo-2-naphthol is available for use as the starting material (in which case a small catalytically effective amount of an acidic catalyst, most preferably hydrogen bromide, is introduced into the reaction mixture) to ensure initiation of the reaction. From then on it particularly preferred, and important when seeking the best results achievable from the practice of this invention, to control the amount of hydrogen bromide by-product remaining in the liquid phase by purging the reaction mixture with hydrogen or an inert gas such as nitrogen, argon, neon, etc., so that most of the by-product hydrogen bromide is continuously removed as it is formed while still leaving a small catalytically effective amount of hydrogen bromide dissolved in the liquid reaction medium. The rate of purging is best determined in any given situation by running a few pilot experiments and determining by analysis of the product, the amount of "overhydrodebrominated" product that exists in the product. If too much hydrogen bromide is left in the product, the amount of non-brominated 2-naphthol will become excessive. Conversely, if too little hydrogen bromide is left in the liquid phase, incomplete reactions with excessive amounts of brominated products will result. Thus the rate of purge is controlled such that the recovered 6-bromo-2-naphthol product on completion of the regioselective hydrodebromination contains no more than about 1 wt % (preferably no more than about 0.5 wt %) of non-brominated 2-naphthol, and no more than about 5 wt % (preferably no more than about 1 wt %) of ar-polybromo impurities. Most preferably the recovered 6-bromo-2-naphthol product on completion of the regioselective hydrodebromination contains no more than about 0.5 wt % of non-brominated impurities, and no more than about 1 wt % of polybromo impurities.

The best way of performing the controlled purge of by-product hydrogen bromide from the reaction mixture is to sparge the reaction mixture with hydrogen throughout substantially the entire hydrodebromination reaction period. In this operation the hydrogen should be continuously introduced into the lowermost portion of the reaction mixture so that it sweeps through substantially the entire reaction mixture and the resultant vapors should be continuously removed from the headspace above the reaction mixture at a rate sufficient to keep the gaseous input to and output from the reaction in a substantially equilibrium condition. Thus reactors equipped with sparger inlets at their lower interiors and gaseous offtake outlets at their upper interiors are preferably employed. The gaseous mixture of hydrogen and entrained hydrogen bromide is preferably passed through a scrubber system containing water and/or a suitable base, e.g., aqueous sodium hydroxide, to remove the hydrogen bromide from the hydrogen so that the hydrogen can be recycled continuously in the purging operation.

Thus a preferred way of producing 6-bromo-2-naphthol pursuant to this invention is a process that comprises reacting 1,6-dibromo-2-naphthol with hydrogen or a precursor compotmd that generates nascent hydrogen in the medium of the reaction, in a halogen-containing liquid solvent comprising at least about 50% (most preferably over 95%) by weight of (a) at least one liquid organic halide solvent in which the halogen content has an atomic number of 35 or less (especially ethylene dichloride) or (b) a solvent mixture consisting essentially (e.g., at least about 90% and most preferably over 98%) by weight of the combination of water and at least one such liquid organic halide solvent (especially ethylene dichloride), and in the presence of catalytically effective amounts of (i) a tungsten carbide-based catalyst, and (ii) at least one phase transfer catalyst, and in the presence at the start of the reaction of a small, reaction-initiating amount of an acid, preferably a carboxylic acid or more preferably, a mineral acid or anhydride, most preferably hydrobromic acid or hydrogen bromide, such that 6-bromo-2-naphthol is formed, and substantially continuously purging hydrogen bromide from the reaction mixture substantially as soon as it is formed.

The regiospecific hydrodebromination reaction when conducted with purge of hydrogen bromide from the reaction mixture is typically conducted at temperatures in the range of about 50 to about 150° C. at pressures in the range of about 65 to about 200 psig, and preferably at temperatures in the range of about 90 to about 120° C. at pressures in the range of about 65 to about 120 psig.

If a purge of hydrogen bromide is not used, the only presently known way of achieving satisfactory results is to perform the reaction at relatively high temperatures and pressures (e.g., 100 to 300° C. at 500 to 1500 psig).

Upon completion of the regioselective hydrodebromination reaction, the organic halide solvent is removed from the 6-bromo-2-naphthol formed in the reaction so that the 6-bromo-2-naphthol is at least substantially completely free from any halogen-containing impurity content. A preferred way of effecting this separation involves (i) adjusting the pH of the reaction mixture to approximately 7 to thereby prevent or at least markedly suppress isomerization or disproportionation of the product(s) in the reaction mixture, (ii) distilling off most of the organic halide solvent from the reaction mixture, (iii) adding water to the reaction mixture, and then (iv) distilling off the remainder of the organic halide solvent azeotropically with water, and keeping the temperature of the reaction mixture below 100° C. when conducting each of these operations. This method has proven exceptionally effective when using ethylene dichloride as the organic halide of the liquid reaction medium. As those skilled in the art can readily appreciate, the initial amount of organic halide distilled off, and the amount of water added to the residual mixture for use in conducting the azeotropic distillation are largely discretionary, involve the use of common sense, and can be readily optimized for any given set of circumstances. As a point of reference, if the liquid reaction medium is composed solely of ethylene dichloride, the initial distillation will typically remove from 85 to 95 percent of the ethylene dichloride, and the amount of water added will typically be about 10 to about 20 wt % of the original ethylene dichloride, or about 80 to about 120 wt % of the ethylene dichloride remaining in the reaction product.

To illustrate preferred procedures for conducting the regioselective hydrodebromination reaction in accordance with this invention, the following non-limiting examples are presented. In these examples four basic general procedures were used. In Examples 8–14 (Table 1) catalytic hydrodebromination was conducted per this invention using tungsten carbide catalyst and a phase transfer co-catalyst without purge of hydrogen bromide. Examples 15–48 (Table 2) were catalytic hydrodebromination reactions conducted per preferred embodiments of this invention using tungsten carbide catalyst, a phase transfer co-catalyst and continuous purge of hydrogen bromide from the reaction mixture during the reaction. Comparative Examples 49–51 (Table 3) and Comparative Examples 52–55 (Table 4) show results achieved when hydrodebromination reactions were conducted using tungsten carbide catalyst but without phase transfer catalyst, and where in Table 3 no purge of hydrogen bromide was used and Table 4 where a purge of hydrogen was used during the reaction.

EXAMPLES 8–14

The general procedure for catalytic hydrodebromination using tungsten carbide catalyst and a phase transfer co-catalyst without purge of hydrogen bromide (Table 1) is as follows: The reactions were conducted in either a 100 or 300 mL Hastalloy B autoclave. For addition of hydrogen, the reactor was equipped with an incoming line to the interior of the reactor, and dip tube therein. Hydrogen pressure was controlled by means of a regulator valve at the gas cylinder. Contents of the reactor were agitated either at 680 rpm or 1700 rpm throughout the reaction. A solution of 1,6-dibromo-2-naphthol (1,6-DBN) in ethylene dichloride (EDC), tungsten carbide catalyst (with average particle size of less than 1 micron) and tetrabutylammonium bromide (TBAB) or in some cases, cetyltrimethylammonium bromide (CTAB) cocatalyst were charged to the reactor. The reactor was then sealed and purged three times with hydrogen. Next, the reactor was pressurized with hydrogen and slowly warmed to the desired reaction temperature. Hydrogen was added as necessary to maintain the pressure at the desired level. Samples were withdrawn periodically to monitor progress of the reaction. At the end of the reaction, the reaction mixture was allowed to settle and the organic layer was decanted or removed through the dip tube. The tungsten carbide catalyst was either used for a second run or washed with solvent and discarded. Conditions and results of representative runs conducted in this manner are summarized in Table 1. Unless otherwise indicated, in each run of Table 1, (a) the tungsten carbide catalyst concentration was 10 wt %, (b) 2.41 grams of 1,6-DBN in 60 mL of EDC (an approximately 0.13 molar solution) was charged to the reactor along with 0.1–0.2 wt % of the co-catalyst, (c) the co-catalyst was TBAB, and (d) reaction was conducted at 500 psi with stirring at 680 rpm. Each example is a single continuous run with analytical results shown on samples withdrawn after various times specified cumulatively in the table. To illustrate, Example 8 was run for 4 hours with samples taken at the end of 0.5, 1, 2, 3, and 4 hours, and conditions were held constant throughout, except that at the start of the 3rd hour of the run the temperature was raised from 100° C. to 125° C. and held there for the next one hour. In the tables, 8-BN is 8-bromonaphthol and 2-NTL is 2-naphthol.

TABLE 1

Hydrodebromination With WC and Phase Transfer Catalysts Without HBr Purge

| Ex. No. | Temp., ° C. | Time, hr | 1,6-DBN, % | 6-BN, % | Others, % | Comments |
|---|---|---|---|---|---|---|
| 8 | 100 | 0.5 | 91.7 | 8.2 | none | (1) |
|  | 100 | 1 | 80.2 | 19.6 | none |  |
|  | 100 | 2 | 60.4 | 33.8 | none |  |
|  | 100 | 3 | 53.0 | 42.1 | none |  |
|  | 125 | 4 | 16.4 | 45.7 | 2-NTL, 18.8 |  |
| 9 | 110 | 1 | 36.5 | 52.6 | 2-NTL, 2.0 | (1) |
|  | 110 | 2 | 14.3 | 52.6 | 2-NTL, 16.3 |  |
|  | 110 | 3 | 8.2 | 44.5 | 2-NTL, 35.7 |  |
| 10 | 105 | 0.5 | 67.5 | 30.5 |  | (1) |
|  | 105 | 1 | 50.6 | 43.6 | 2-NTL, 0.6 |  |
|  | 105 | 1.5 | 39.9 | 48.7 | 2-NTL, 4.8 |  |
|  | 105 | 2 | 28.9 | 51.9 | 2-NTL, 10.4 |  |
|  | 105 | 2.5 | 20.3 | 52.9 | 2-NTL, 15.7 |  |
|  | 105 | 3 | 13.4 | 52.9 | 2-NTL, 22.5 |  |
| 11 | 103 | 0.5 | 40.9 | 59.1 | none | (1),(2) |
|  | 103 | 1 | 18.1 | 80.9 | none |  |
|  | 103 | 1.5 | 10.0 | 88.9 | none |  |
|  | 103 | 2 | 5.5 | 90.7 | none |  |
|  | 103 | 2.5 | 1.4 | 88.3 | 2-NTL, 4.4 |  |
| 12 | 103 | 0.5 | 40.8 | 54.3 | none | (1),(3) |
|  | 103 | 1 | 19.5 | 73.5 | 2-NTL, 1.8 |  |

TABLE 1-continued

Hydrodebromination With WC and Phase Transfer Catalysts Without HBr Purge

| Ex. No. | Temp., °C. | Time, hr | 1,6-DBN, % | 6-BN, % | Others, % | Comments |
|---|---|---|---|---|---|---|
|  | 103 | 1.5 | 11.0 | 78.8 | 2-NTL, 5.0 |  |
|  | 103 | 2 | 6.8 | 78.5 | 2-NTL, 10.2 |  |
|  | 103 | 2.5 | 4.3 | 76.9 | 2-NTL, 15.1 |  |
| 13 | 130 | 5 | 0.7 | 67.6 | 2-NTL, 25.8; others, 5.9 | (1),(4) |
| 14 | 110 | 2.5 | 1.5 | 81.3 | 2-NTL, 6.4; others, 10.8 | (1),(4) |

(1) The amount of HBr at the start of the reaction was not measured; However, the initial EDC solvent was saturated with or at least contained sufficient HBr to initiate the reaction.
(2) In this example, the starting solution was 18 wt % of 1,6-DBN in EDC.
(3) In this example, the starting solution was 29 wt % of 1,6-DBN in EDC.
(4) In this example, 20 wt % of tungsten carbide catalyst, a 30 wt % solution of 1,6-DBN in EDC, and 0.2 gram of CTAB co-catalyst were used; the pressure was 250 psi and the mixture was stirred at 1700 rpm.

EXAMPLES 15–48

In the examples given in Table 2, the general procedure of the examples of Table 1 was used except that pursuant to a preferred embodiment of this invention this catalytic hydrodebromination with tungsten carbide and phase transfer catalysts was conducted with a continuous purge of hydrogen bromide from the reactor throughout the reaction. Hydrogen was used as the purging gas and the purge stream of off-gases from the reaction was passed into a caustic scrubber, while keeping the internal pressure in the reactor at the desired level by the continuous introduction of fresh hydrogen. For effecting the purge, a valve was connected to the head-space of the reactor. Connected to this valve was ¼-inch polytetrafluoroethylene tubing which directed the purge stream through a knockout pot and thence into two 20 wt % caustic solutions arranged in series. After the gas passed through the scrubbers, it was passed through a wet test meter filled with Varsol. Readings from the wet test meter were recorded to control the incoming flow of fresh hydrogen into the reactor.

TABLE 2

Hydrodebromination With WC and Phase Transfer Catalysts and With HBr Purge

| Ex. No. | DBN, wt % | WC, wt % | Co-catalyst, wt % | Temp. °C. | Pressure, psig | Time, hr | 1,6-DBN, % | 6-BN, % | Others, % | Comments |
|---|---|---|---|---|---|---|---|---|---|---|
| 15 | 30 | 20 | CTAB, 1.5 | 100 | 90 | 6 | 0.2 | 88.5 | 2-NTL, 2.6 |  |
| 16 | 30 | 20 | CTAB, 2 | 100 | 90 | 5 | 0.3 | 82 | 2-NTL, 6.5 |  |
| 17 | 30 | 17 | TBAB, 2 | 100 | 90 | 7 | 0.6 | 83.5 | 2-NTL, 10.3 |  |
| 18 | 30 | 17 | TBAB, 1 | 110 | 90 | 5 | 0.2 | 87.7 | 2-NTL, 5.1 |  |
| 19 | 33 | 20 | TBAB, 0.5 | 115 | 90 | 5 | 0.3 | 89.6 | 2-NTL, 2.7 |  |
| 20 | 33 | 20 | TBAB, 0.2 | 115 | 90 | 6 | 0.6 | 91 | 2-NTL, 1.1 |  |
| 21 | 30 | 20 | TBAB, 0.25 | 115 | 95 | 5.5 | 0.6 | 94.7 | 2-NTL, 1.5 |  |
| 22 | 34 | 20 | TBAB, 0.1 | 115 | 62 | 7 | 0.4 | 91.3 | 2-NTL, 0.3 |  |
| 23 | 34 | 30 | TBAB, 0.1 | 115 | 63 | 6 | 0.1 | 88 | 2-NTL, 0.7 | (1) 1.6 |
| 24 | 34 | 30 | TBAB, 0.1 | 125 | 125 | 2 | 0.5 | 83 | 2-NTL, 3.7 | (1) 2.3 |
| 25 | 44 | 20 | TBAB, 0.1 | 115 | 300 | 2 | 0.4 | 55 | 2-NTL, 21.2 | (1) 14.8, (7) |
| 26 | 34 | 20 | TBAB, 0.1 | 115 | 300 | 2 | 0.2 | 81.8 | 2-NTL, 4.6 | (1) 4.2 |
| 27 | 34 | 20 | TBAB, 0.1 | 115 | 300 | 2 | 0.1 | 88 | 2-NTL, 2.7 | (1) 2.1 |
| 28 | 34 | 30 | TBAB, 0.1 | 90 | 125 | 4.5 | 0.4 | 84.2 | 2-NTL, 3.2 |  |
| 29 | 34 | 30 | TBAB, 0.1 | 90 | 125 | 5.5 | 0.4 | 90.2 | 2-NTL, 0.5 | (7) |
| 30 | 44 | 30 | TBAB, 0.1 | 90 | 125 | 4 | 0.5 | 88.6 | 2-NTL, 1.3 | (7) |
| 31 | 33 | 30 | TBAB, 0.1 | 90 | 125 | 7 | 2.8 | 84.6 | 2-NTL, 1.0 | (7) |
| 32 | 33 | 30 | TBAB, 0.1 | 90 | 125 | 6 | 0.6 | 89.5 | 2-NTL, 1.7 | (7) |
| 33 | 33 | 30 | TBAB, 0.1 | 90 | 125 | 6 | 1.2 | 85.3 | 2-NTL, 1.5 | (2),(7) |
| 34 | 34 | 30 | TBAB, 0.1 | 90 | 125 | 4 | 2.1 | 54.4 | 2-NTL, 21.5 | (3),(7) |
| 35 | 38 | 30 | TBAB, 0.1 | 90 | 125 | 8 | 1.3 | 77.9 | 2-NTL, 0.6 | (4) |
| 36 | 33 | 30 | TBAB, 0.1 | 90 | 125 | 1.5 | 3.4 | 76.9 | 2-NTL, 6.4 | (5),(7) |
| 37 | 33 | 30 | TBAB, 0.1 | 90 | 125 | 2 | 1.1 | 83.2 | 2-NTL, 3.2 | (5),(7) |
| 38 | 33 | 30 | TBAB, 0.1 | 115 | 125 | 2 | 0.4 | 85.3 | 2-NTL, 1.5 | (7) |
| 39 | 33 | 30 | TBAB, 0.1 | 115 | 125 | 3.5 | 0.6 | 87.8 | 2-NTL, 0.5 | (7) |
| 40 | 33 | 30 | TBAB, 0.1 | 115 | 127 | 1 | 0.7 | 85.2 | 2-NTL, 4.0 | (7) |
| 41 | 33 | 30 | TBAB, 0.1 | 115 | 127 | 3 | 0.3 | 86.9 | 2-NTL, 2.1 | (7) |
| 42 | 33 | 30 | TBAB, 0.1 | 115 | 127 | 3 | 0.3 | 88.5 | 2-NTL, 0.5 | (7) |
| 43 | 33 | 30 | TBAB, 0.1 | 115 | 127 | 3 | 56.6 | 33.7 | 2-NTL, 0.1 | (7) |
| 44 | 33 | 30 | TBAB, 0.1 | 115 | 127 | 3 | 0.3 | 89.3 | 2-NTL, 1.4 | (7) |
| 45 | 33 | 30 | TBAB, 0.1 | 115 | 127 | 1 | 3.8 | 82.6 | 2-NTL, 3.5 | (6),(7) |
| 46 | 34 | 30 | TBAB, 0.1 | 115 | 127 | 1 | 0.3 | 90.6 | 2-NTL, 6.1 | (7) |
| 47 | 34 | 30 | TBAB, 0.1 | 115 | 127 | 0.5 | 0.6 | 87.4 | 2-NTL, 1.1 | (7) |
| 48 | 33 | 30 | TBAB, 0.1 | 115 | 93 | 3 | 0.5 | 87.1 | 2-NTL, 2.4 | (7) |

(1) Other impurities were detected in the amount shown.
(2) 48% HBr was added before the start of the reaction.
(3) Anhydrous HBr was added before the start of the reaction.
(4) Additional EDC was added during the reaction as makeup for purged EDC.
(5) The reactor was vented during the reaction.
(6) Acetic acid was added to the initial solution of 1,6-DBN in EDC to initiate the reaction.
(7) The solvent used was a mixture of EDC and water.

COMPARATIVE EXAMPLES 49–55

Except as otherwise indicated in Tables 3 and 4, the comparative runs summarized therein were conducted in comparable manner to those of Tables 1 and 2 except that the runs of Table 3 had no transfer catalyst and no purge of HBr whereas the runs of Table 4 did have HBr purge but no phase transfer catalyst.

TABLE 3

Hydrodebromination With WC but Without Phase Transfer Catalyst and Without HBr Purge

| Ex. No. | HBr, g | Temp., °C. | Time, hr | 1,6-DBN, % | 6-BN, % | Others, % | Comments |
|---|---|---|---|---|---|---|---|
| 49 | 0.64 | 150 | 1 | 93.4 | 6.6 | none | (1) |
|  |  | 150 | 3 | 83.8 | 16.2 | none |  |
|  |  | 150 | 4 | 46.0 | 54.0 | none |  |
|  |  | 250 | 5.5 | 19.8 | 75.2 | 8-BN, 5.0 |  |
| 50 |  | 150 | 0.5 | 59.3 | 40.5 |  | (2),(3) |
|  |  | 150 | 1 | 35.8 | 64.2 | 2-NTL, 1.5 |  |
|  |  | 150 | 2 | 14.9 | 81.6 | 2-NTL, 2.6 |  |
|  |  | 150 | 3 | 3.9 | 82.6 | 2-NTL, 7.2 |  |
|  |  | 150 | 4 | 1.5 | 83.1 | 2-NTL, 14.8 |  |
| 51 |  | 100 | 0.5 | 73.9 | 20.8 | 2-NTL, 5.3 | (2),(4) |
|  |  | 100 | 1 | 55.7 | 38.7 | 2-NTL, 5.7 |  |
|  |  | 100 | 1.5 | 37.2 | 55.9 | 2-NTL, 7.0 |  |
|  |  | 100 | 2 | 22.2 | 69.3 | 2-NTL, 2.0 |  |
|  |  | 100 | 2.5 | 10.8 | 77.6 | 2-NTL, 4.7 |  |
|  |  | 100 | 3 | 5.5 | 78.4 | 2-NTL, 7.9 |  |
|  |  | 100 | 3.5 | 2.1 | 70.1 | 2-NTL, 12.2 |  |
|  |  | 100 | 4 | 2.0 | 70.1 | 2-NTL, 9.1 |  |

(1) In this example, 48% aqueous HBr was added to the initial solution of 1,6-DBN in EDC.
(2) The amount of HBr at the start of the reaction was not measured; However, the initial EDC solvent was saturated or at least contained sufficient HBr to initiate the reaction.
(3) In this example, the starting solution was 29 wt % of 1,6-DBN in EDC.
(4) In this example, 108 mL of EDC was used as the solvent/diluent.

TABLE 4

Hydrodebromination With WC and With Purge but Without Phase Transfer Catalyst

| Ex. No. | DBN, wt % | Solvent | WC, wt % | Temp. °C. | Pressure, psig | Time, hr | 1,6-DBN, % | 6-BN, % | Others, % |
|---|---|---|---|---|---|---|---|---|---|
| 52 | 34 | EDC | 20 | 110 | 62 | 5 | 57.1 | 32.3 | 2-NTL, 0.1 |
| 53 | 44 | EDC/H$_2$O | 20 | 115 | 300 | 1.5 | 0.6 | 58.2 | 2-NTL, 20.1 |
| 54 | 33 | EDC/H$_2$O | 15 | 90 | 125 | 3 | 9.4 | 75.0 | –2-NTL, 2.4 |
| 55 | 33 | EDC/H$_2$O | 30 | 115 | 127 | 3.5 | 0.8 | 80.5 | 2-NTL, 7.2 |

Three-Stage Process for Producing 2-Bromo-6-methoxynaphthalene

A preferred synthesis process for producing 2-bromo-6-methoxynaphthalene in accordance with this invention involves three main reactions, together with particular separation and purification procedures. A detailed procedure for performing this operation is as follows: A first step (assuming 1,6-dibromo-2-naphthol of suitable purity is not commercially available at an attractive price) involves forming 1,6-dibromo-2-naphthol by brominating 2-naphthol in ethylene dichloride, or in a mixture of ethylene dichloride (EDC) and water using a phase transfer catalyst such as described in U.S. Pat. No. 5,426,243. On completion of the reaction the aqueous phase is separated from the organic phase by decantation. Then tungsten carbide of about 0.9 micron average particle size (about 6 to 12 wt % of the total weight of the resulting mixture) and TBAB (about 0.02 to 0.05 wt % based on the total weight of the resulting mixture) are added to the organic phase. This mixture is then selectively hydrodebrominated with continuous hydrogen purge at 60 to 90 psig at 100° C. to 110° C. for 4 to 8 hours with constant agitation of the reaction mixture to ensure intimate contact among the three phases in the system. Then the reaction product mixture is allowed to stand long enough for the solids to settle, and the liquid phase is separated from the solids by decantation. The EDC solution is then neutralized with aqueous caustic solution. Most of the EDC is flashed off or removed by distillation, water is added to the product residue, and the remainder of the EDC is removed therefrom by azeotropic distillation with water. 2-Propanol is added to the EDC-freed, molten 6-bromo-2-naphthol product residue in proportions by weight of about 3:1, respectively. Next, sodium hydroxide (about 10 mol % excess based on 6-bromo-2-naphthol) and methyl chloride (about 20 mol % excess relative to 6-bromo-2-naphthol) are charged to the reactor containing the 2-propanol and EDC-freed product mixture. The resultant mixture is heated to about 70 to about 90° C. for about 3 to about 5 hours with constant agitation. Then the 2-propanol is stripped off, and the residue while hot enough to keep the 2-bromo-6-methoxynaphthalene in molten condition (e.g., 90 to 112° C.) is washed with water (under superatmospheric pressure, if necessary) and the washings are discarded. The washed product is then subjected to distillation (about 160 to 165° C. at 1 mmHg) to recover purified 2-bromo-6-methoxynaphthalene. Then the purified 2-bromo-6-methoxynaphthalene is dissolved in and crystallized from 2-propanol at 10° C. to yield 2-bromo-6-methoxynaphthalene in highly purified, white crystalline form.

Production of Nabumetone and Precursors Thereof (A) Preparation of 4-(6'-Methoxy-2'-Naphthyl)-3-Buten-2-one, a Precursor of Nabumetone One embodiment of this invention comprises preparing 2-bromo-6-methoxynaphthalene as described herein and then contacting the 2-bromo-6-methoxynaphthalene so-formed with methylvinylketone (3-buten-2-one) in the presence of a palladium (II) catalyst at a temperature of from about 50° C. to about 200° C. for a time sufficient to cause reaction such that 4-(6'-methoxy-2'-naphthyl)-3-buten-2-one, a precursor of nabumetone is formed. The reaction between the 2-bromo-6-methoxynaphthalene and the methylvinylketone is preferably conducted in a liquid solvent for the reactants and the catalyst used, and for a time sufficient for substantially complete reaction to occur, which typically is in the range of from about 0.25 to about 10 hours. One or more reaction temperatures are usually in the range of about 50° C. to about 200° C., preferably in the range of about 75° C. to about 150° C., and most preferably in the range of about 120° C. to about 150° C. One preferred palladium (II) catalyst in the form introduced into the mixture in which the reaction is to occur is dichlorobis(triphenylphosphine) palladium (II). Other palladium (II) catalysts, and complete details for conducting this reaction, are set forth in U.S. Pat. No. 5,225,603 (Jul. 6, 1993) to M. Aslam and V. Elango, the entire disclosure of which is incorporated herein by reference. In addition to the two Examples of the foregoing patent to M. Aslam and V. Elango modified only to the extent that the 2-bromo-6-methoxynaphthalene thereof is prepared as described herein in Example 7 hereof, the following additional Example 56 is presented. It is based in part on procedures described by M. Aslam, V. Elango, and K. G. Davenport, *Synthesis*, 1989, (November Issue) 869–870).

EXAMPLE 56

A mixture of 2-bromo-6-methoxynaphthalene prepared as in Example 7 hereof (5.92 grams, 25 mmol), 3-buten-2-one (2.1 grams, 30 mmol), bis(triphenylphosphine)palladium(II) chloride, $(Ph_3P)_2PdCl_2$, (0.32 gram, 0.45 mmol), and sodium bicarbonate (2.5 grams, 30 mmol), in 1-methyl-pyrrolidinone (NMP, 60 mL) is sealed in an autoclave. The autoclave is purged with nitrogen and the mixture placed under a nitrogen atmosphere (1.7 bar) and heated at 130° C. for 3 hours. The autoclave is cooled, depressurized and the contents are added to water (500 mL). The ensuing solid is collected by filtration and dissolved in methylene dichloride (150 mL). The methylene dichloride solution is dried $(MgSO_4)$ and filtered through a Celite pad. Concentration of the filtrate affords 4-(6'-methoxy-2'-naphthyl)-3-buten-2-one as a solid. The product is purified by crystallization from ethanol to afford white crystals which melt at about 120–121° C.

(B) Preparation of Nabumetone via 4-(6'-Methoxy-2'-Naphthyl)-3-Buten-2-one as an Intermediate In this embodiment 4-(6'-methoxy-2'-naphthyl)-3-buten-2-one formed as in (A) above is hydrogenated with hydrogen, preferably using a hydrogenation catalyst such as palladium on charcoal or other known hydrogenation catalysts. Such hydrogenation procedures can be carried out in an inert organic solvent at ambient temperature or slightly superatmospheric pressure. Suitable procedures for conducting the catalytic hydrogenation of 4-(6'-methoxy-2-naphthyl)-3-butene-2-one which may be used in the practice of this embodiment are described in the prior art such as, for example, in U.S. Pat. No. 4,061,779 (Dec. 6, 1977) to A. W. Lake and C. J. Rose; U.S. Pat. No. 4,221,741 (Sep. 9, 1980) to L. M. Gaster; and U.S. Pat. No. 5,225,603 (Jul. 6, 1993) to M. Aslam and V. Elango, the entire disclosures of each of which relating to the conduct of hydrogenations are incorporated herein by reference. Although the starting material for the hydrogenations described in the foregoing patent to L. M. Gaster is 4-(6'-methoxy-2'-naphthyl)-4-hydroxy-3-buten-2-one, the descriptions given therein relating to hydrogenation are directly translatable to the hydrogenation of 4-(6'-methoxy-2'-naphthyl)-3-buten-2-one.

(C) Preparation of 6-Methoxy-2-Naphthaldehyde, a Precursor of Nabumetone Another embodiment of this invention comprises preparing 2-bromo-6-methoxynaphthalene as to described herein, converting the 2-bromo-6-methoxynaphthalene into a Grignard reagent, and reacting the Grignard reagent with N,N-dimethylformamide (DMF) which yields after workup, 6-methoxy-2-naphthaldehyde. The Grignard reagent is formed by adding finely divided magnesium and, optionally a crystal of iodine, to a solution of 2-bromo-6-methoxynaphthalene in a suitable ether, such as diethyl ether or tetrahydrofuran in a dry, inert environment, and stirring the mixture at a temperature in the range of about 25 to about 80° C. The reaction of the resultant Grignard reagent with DMF is preferably conducted by adding the DMF portionwise to the Grignard reagent while stirring the mixture at a temperature in the range of about 25 to about 100° C., followed by acid hydrolysis. The following Example 57 is based in part on the procedure of A. Horeau, J. Jacques and R. Émiliozzi, *Bull. Soc. Chim. Fr.* 1959, at page 1857.

EXAMPLE 57

To a reactor equipped with a stirrer are charged 10 grams of 2-bromo-6-methoxynaphthalene prepared as in Example 7 hereof, 1.05 grams of magnesium and 35 mL of tetrahydrofuran (THF). The reaction is initiated by addition of a crystal of iodine. After one hour of heating at reflux with stirring, 10 mL of DMF mixed with 10 mL of THF is added and the mixture is again refluxed with stirring for 1.5 hours. The reaction mixture is hydrolyzed by addition of dilute acetic acid and a precipitate of crude 6-methoxy-2-naphthaldehyde is formed. The precipitate is recovered by filtration, washed with water, and purified by crystallization from methanol.

(D) Preparation of 4-(6'-Methoxy-2'-Naphthyl)-3-Buten-2-one. a Precursor of Nabumetone In this embodiment 6-methoxy-2-naphthaldehyde prepared as in (C) above is subjected to a base-catalyzed aldol condensation with acetone to form 4-(6'-methoxy-2'-naphthyl)-3-buten-2-one. This reaction is typically conducted in acetone using aqueous inorganic base such as a 10% aqueous solution formed by adding sodium hydroxide, sodium oxide, potassium hydroxide or potassium oxide to water. The reaction can be conducted at temperatures within the range of about 0 to about 60° C., and typically is performed at ambient room temperature. The reaction mixture is stirred or otherwise agitated. A reaction period of several hours is usually sufficient. Product workup typically involves acidifying the reaction solution, extracting with ether, drying the ether solution and then evaporating the ether to yield the desired product. Procedural details for conducting such a reaction are given, for example, in U.S. Pat. No. 4,061,779 (Dec. 6, 1977) to A. W. Lake and C. J. Rose, the entire disclosure of which relating to this aldol condensation reaction is incorporated herein by reference. The following Example 58 is based in part on the procedure of given by A. C. Goudie, L. M. Gaster, A. W. Lake, C. J. Rose, P. C. Freeman, B. O. Hughes and D. Miller, *Journal of Medicinal Chemistry*, 1978, at pages 1262–3. This entire paper of Goudie et al.

(op. cit., pages 1260–1264), is incorporated herein by reference as regards all synthesis procedures in which 2-bromo-6-methoxynaphthalene can be used as a reactant in forming a precursor of nabumetone.

EXAMPLE 58

A mixture of 6-methoxy-2-naphthaldehyde prepared as in Example 57 hereof, (30 grams, 0.16 mol), acetone (500 mL) and 10% aqueous NaOH (10 mL) is stirred for 3 hours before being acidified with concentrated HCI and extracted with diethyl ether. The ether extract is dried ($MgSO_4$) and evaporated to yield a solid which is purified on a silica gel column using benzene as eluant. The 4-(6'-methoxy-2'-naphthyl)-3-buten-2-one is recovered as a pale-yellow solid with a melting point of about 120° C.

(E) Preparation of Nabumetone via 4-(6'-Methoxy -2'-Naphthyl)-3-Buten-2-one, as an Intermediate In this embodiment 4-(6'-methoxy-2'-naphthyl)-3-buten-2-one formed as in (D) above is hydrogenated with hydrogen, preferably using a hydrogenation catalyst such as palladium on charcoal or other known hydrogenation catalysts. For further details, the reader is referred to (B) above, and the references cited therein.

(F) Preparation of Nabumetone by Catalyzed Direct Reaction of 2-Bromo-6-Methoxynaphthalene with 3-Buten-2-ol Another embodiment of this invention comprises preparing 2-bromo-6-methoxynaphthalene as described herein and then reacting the 2-bromo-6-methoxynaphthalene with 3-buten-2-ol in the presence of a catalyst, preferably a catalyst comprising a palladium compound in combination with a ligand comprising trivalent phosphorus. Examples of such catalysts include palladium (II) acetate in combination with triphenyl phosphine or a bis(triphenylphosphine) dichloropalladium (II) complex. The reaction is typically carried out at one or more temperatures in the range of about 50 to about 200° C., preferably at one or more temperatures in the range of about 75 to about 175° C., and most preferably at one or more temperatures in the range of about 120 to about 150° C. for a time sufficient for substantially complete reaction to occur, which typically is in the range of from about 0.25 to about 10 hours. Preferably the reaction is conducted for a period of about 3 to about 6 hours.

The catalyst for the reaction is preferably, but not necessarily, a palladium compound complexed with at least one ligand comprising trivalent phosphorus. Some palladium catalysts which may be used wherein the palladium is complexed with an appropriate ligand are such complexes of palladium as:

bis(triphenylphosphine)dichloro palladium (II);
bis(tributylphosphine)dichloro palladium (II);
bis(tricyclohexylphosphine)dichloro palladium (II);
pi-allyltriphenylphosphinedichloro palladium (II);
triphenylphosphinepiperidinedichloro palladium (II);
dichlorobis(cyclohexanone oxime) palladium (II) 1,5,9-cyclododecatrienedichloro palladium (II);
dicarbonylbis(triphenylphosphine) palladium (0) bis(triphenylphosphine)diacetate palladium (II);
bis(triphenylphosphine)sulfate palladium (II);
bis(2,4-pentanedionatopalladium) (II); and
tetrakis(triphenylphosphine) palladium (0).

The palladium salts and phosphine ligands making up the foregoing catalyst complexes may also be added separately to the reaction zone. In this case, the amount of ligand added is preferably sufficient to complex with the palladium present such that the P:Pd mole ratio is equal to at least about 1:1 and may be as high as, for example, about 10:1. Preferably the P:Pd ratio is in the range of about 0.5:1 to 2:1. Salts of palladium (II) which may be utilized separately with the ligand are, for example, palladium (II) nitrate, chloride, acetate, bromide, sulfate and the like.

The reactants, 3-buten-2-ol and 2 bromo-6-methoxynaphthalenie, may be mixed in equimolar quantities, or either one of the reactants may be used in excess. Preferably, an excess, typically of about 5 to 50% of the 3-buten-2-ol is used to drive the reaction to completion.

An equimolar quantity of the palladium catalyst may be used or, preferably, a lesser amount may be used in the presence of a compound which will regenerate the active catalyst during the reaction. Typically, from about 0.01 to about 0.1 molar amount of catalyst per mole of reactant is used.

Regeneration of the catalyst during reaction is accomplished by addition of an excess of base. As used in this description, a base is a compound which reacts with the hydrogen bromide formed in the reaction regenerating the catalyst and causing formation of an inert material. Such compounds include, for example, alkali metal bicarbonates and carbonates such as sodium bicarbonate, sodium carbonate, potassium bicarbonate, and potassium carbonate, and organic amines such as triethylamine, diethylamine, tripropylamine, and dipropylamine. The base may be used in an amount, for example, of about 1 to 5 mol per mole of 2-bromo-6-methoxynaphthalene. The preferred base is sodium bicarbonate which reacts with the hydrogen bromide to form carbon dioxide, water, and the active catalyst. The carbon dioxide and water are inert and are easily separable from the reaction solution on isolation of the product.

The reaction may be carried out without a solvent, or in an inert liquid solvent. Solvents which can be used include, for example, nitrites, amides, and ethers, e.g., N-methyl pyrrolidinone, acetonitrile, dimethyl sulfoxide, dimethyl formamide, dimethyl acetamide, tetrahydrofuran, and the like. The amount of solvent, if used, may be such that the weight ratio of solvent to total reaction mass, exclusive of the solvent, is up to about 5:1, preferably about 2:1.

The reaction is carried out in an inert atmosphere to avoid oxidation and by-product formation. Typically a nitrogen, argon, or helium atmosphere is used for the reaction.

The nabumetone product may be isolated from the reaction mixture by methods known in the art. Typically, the reaction mixture may be poured into water at which time the product is separated as a crystalline solid. The solid may be crystallized to give a pure crystalline material melting at about 80° C.

The following examples further illustrate this procedure:

EXAMPLE 59

A mixture of 2-bromo-6-methoxynaphthalene produced as in Example 7 hereof (2.37 grams, 10 mmol), 3-buten-2-ol (1.08 grams, 15 mmol), palladium (II) acetate (0.02 grams, 0.09 mmol), triphenylphosphine (0.047 grams, 0.18 mmol), and sodium bicarbonate (1.0 grams, 12 mmol) in N-methylpyrrolidinone (10 mL) is heated at 140° C.–145° C. under an inert atmosphere for 5 hours. At the end of the heating cycle, the reaction mixture is cooled to room temperature and poured into water to precipitate a solid. The solid is redissolved in dichloromethane (50 mL) and filtered through a Celite pad to remove undissolved material. Concentration of the organic filtrate gives a solid (1.8 grams). GC analysis of the crude product indicates good conversion and formation of a good yield of nabumetone.

EXAMPLE 60

A mixture of 2-bromo-6-methoxynaphthalene formed as in Example 7 hereof (2.37 grams, 10 mmol), 3-buten-2-ol (1.08 grams, 15 mmol), bis(triphenylphosphine)dichloro palladium (II) complex (0.13 grams, 0.18 mol), and sodium bicarbonate (1.0 grams, 12 mmol) in N-methylpyrrolidinone (10 mL) is heated at 140° C. under an inert atmosphere for 5 hours. At the end of the heating cycle, the reaction mixture is cooled to room temperature and poured in water (150 mL) to precipitate a solid. The solid is redissolved in dichloromethane (100 mL) and filtered through a Celite pad to remove undissolved material. Concentration of the filtrate results in formation of a solid. GC-analysis of this crude product confirms the presence therein of nabumetone in good yield.

(G) Preparation of 4-(6'-Methoxy-2'-Naphthyl)-3-Buten-2-ol a Precursor of Nabumetone A further embodiment of this invention comprises preparing 2-bromo-6-methoxynaphthalene as described herein and then contacting the 2-bromo-6-methoxynaphthalene so-formed with 3-buten-2-ol in the presence of a palladium (II) catalyst at a temperature of from about 50° C. to about 200° C. for a time sufficient to cause reaction such that 4-(6'-methoxy-2'-naphthyl)-3-buten-2-ol, a precursor of nabumetone is formed. The reaction between the 2-bromo-6-methoxynaphthalene and the 3-buten-2-ol is preferably conducted in a liquid solvent for the reactants and the catalyst used, and for a time sufficient for substantially complete reaction to occur, which typically is in the range of from about 0.25 to about 10 hours. One or more reaction temperatures are usually in the range of about 50° C. to about 200° C., preferably in the range of about 75° C. to about 150° C., and most preferably in the range of about 120° C. to about 150° C. One preferred palladium (II) catalyst in the form introduced into the mixture in which the reaction is to occur is dichlorobis(triphenylphosphine) palladium (II). Other palladium (II) catalysts that can be used for conducting this reaction are set forth in U.S. Pat. No. 5,225,603 (Jul. 6, 1993) to M. Aslam and V. Elango, the entire disclosure of is incorporated herein by reference. The following Example 61 illustrates this embodiment of the invention. It is based in part on procedures described by M. Aslam, V. Elango, and K. G. Davenport, *Synthesis*, 1989, (November Issue) 869–870.

EXAMPLE 61

A mixture of 2-bromo-6-methoxynaphthalene prepared as in Example 7 hereof (2.37 grams, 10 mmol), 3-buten-2-ol (1.08 grams, 15 mmol), $(Ph_3P)_2PdCl_2$ (0.13 grams, 0.18 mmol) and $NaHCO_3$ (1.0 grams, 12 mmol) in 1-methyl-2-pyrrolidinone (10 mL) is heated at 140° C. under a nitrogen atmosphere for 5 hours. After cooling to room temperature, addition of the mixture to water causes formation of a precipitate. The mixture is filtered and the solid is dissolved in $CH_2Cl_2$ (100 mL). The $CH_2Cl_2$ solution is dried ($MgSO_4$) and filtered through a Celite pad. Concentration of the filtrate affords a solid (1.9 grams). GC analysis of the crude product confirms the presence of 4-(6'-methoxy-2'-naphthyl)-2-butanol. The crude product is purified by crystallization using a 95:5 mixture of hexane and diethyl ether.

(H) Preparation of Nabumetone via 4-(6'-Methoxy-2'-Naphthyl)-3-Buten-2-one as an Intermediate In this embodiment 4-(6'-methoxy-2'-naphthyl)-3-buten-2-one formed as in (G) above is hydrogenated with hydrogen, preferably using a hydrogenation catalyst such as palladium on charcoal or other known hydrogenation catalysts. For further details, the reader is referred to (B) above, and the references cited therein.

(I) Electrolytic Preparation of 6-Methoxy-2-Naphthaldehyde, a Precursor of Nabumetone Another embodiment of this invention comprises preparing 2-bromo-6-methoxynaphthalene as described herein, and converting the 2-bromo-6-methoxynaphthalene into 6-methoxy-2-naphthaldehyde electrolytically as described in U.S. Pat. No. 4,988,416 (1991) to M. Troupel, S. Sibille, J. Perichon, E. D'Incan and C. Saboureau, the entire disclosure of which is incorporated herein by reference. A preferred procedure involves producing 2-bromo-6-methoxynaphthalene in accordance with Example 7 hereof and then conducting the electrolytic procedure as described in Example 14 of U.S. Pat. No. 4,988,416, incorporated by reference herein.

(J) Preparation of 4-(6'-Methoxy-2'-Naphthyl)-3-Buten-2-one, a Precursor of Nabumetone In this embodiment 6-methoxy-2-naphthaldehyde prepared as in (1) above is subjected to a base-catalyzed aldol condensation with acetone to form 4-(6'-methoxy-2'-naphthyl)-3-buten-2-one. For further details, the reader is referred to (D) above, including Example 58 therein, and the references cited in (D) above.

(K) Preparation of Nabumetone via 4-(6'-Methoxy-2'-Naphthyl)-3-Buten-2-one, as an Intermediate In this embodiment 4-(6'-methoxy-2'-naphthyl)-3-buten-2-one formed as in (J) above is hydrogenated with hydrogen, preferably using a hydrogenation catalyst such as palladium on charcoal or other known hydrogenation catalysts. For further details, the reader is referred to (B) above, and the references cited therein.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Without limiting the generality of the foregoing, as an illustrative example, where a claim specifies that a catalyst a palladium compound in combination with a ligand comprising trivalent phosphorus, this phraseology refers to the makeup of the substance before it is mixed with one or more other materials, and in addition, at the time the catalyst is actually performing its catalytic function it need not have its original makeup—instead whatever transformations, if any, that occur in situ as the catalytic reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference for all purposes, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process which comprises:
    a) methylating 6-bromo-2-naphthol with methyl bromide or methyl chloride, or both, in a halogen-free liquid solvent comprising at least 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base such that 2-bromo-6-methoxynaphthalene is formed; and
    b) recovering and purifying 2-bromo-6-methoxynaphthalene so formed.

2. A process according to claim 1 wherein said solvent is at least 98% by weight of at least one alcohol, and wherein the strong base is formed by mixing at least one alkali metal oxide or hydroxide with at least one alcohol.

3. A process according to claim 2 wherein the alkali metal of said oxide or hydroxide is sodium or potassium, or both, and recovery and purification of 2-bromo-6-methoxynaphthalene is effected by a procedure which comprises:
    1) distilling off solvent to leave a hot molten residue;
    2) washing the residue while molten with water to remove alkali metal halide by-product, and water-soluble impurities, if any, from the 2-bromo-6-methoxynaphthalene residue; and
    3) crystallizing the 2-bromo-6-methoxynaphthalene from a liquid medium.

4. A process according to claim 2 wherein the alkali metal of said oxide or hydroxide is sodium or potassium, or both, and recovery and purification of 2-bromo-6-methoxynaphthalene is effected by a procedure which comprises:
    1) distilling off solvent to leave a hot molten residue;
    2) washing the residue while molten with water to remove alkali metal halide by-product, and other water-soluble impurities, if any, from the residue;
    3) distilling 2-bromo-6-methoxynaphthalene from the washed residue; and
    4) crystallizing the 2-bromo-6-methoxynaphthalene from a liquid medium.

5. A process according to claim 4 wherein said crystallization is conducted in 2-propanol.

6. A process according to claim 1 wherein the methylation in a) is conducted using methyl chloride.

7. A process according to claim 6 wherein said solvent is water, or at least one alcohol, or a mixture of water and at least one alcohol.

8. A process according to claim 6 wherein said solvent is 2-propanol, or a mixture of 2-propanol and water.

9. A process according to claim 6 wherein said solvent is at least 98% by weight of at least one alcohol, and wherein tile strong base is formed by mixing at least one alkali metal oxide or hydroxide with at least one alcohol.

10. A process according to claim 9 wherein the alkali metal of said oxide or hydroxide is sodium or potassium, or both, and the recovery and purification of 2-bromo-6-methoxynaphthalene is effected by a procedure which comprises:
    1) distilling off solvent to leave a hot molten residue;
    2) washing the residue while molten with water to remove alkali metal chloride by-product and water-soluble impurities, if any, from the residue;
    3) distilling 2-bromo-6-methoxynaphthalene from the washed residue; and
    4) crystallizing the 2-bromo-6-methoxynaphthalene from a liquid medium.

11. A process according to claim 10 wherein said crystallization is conducted in 2-propanol.

12. A process according to claim 9 wherein the alkali metal of said oxide or hydroxide is sodium or potassium, or both, and the recovery and purification of 2-bromo-6-methoxynaphthalene is effected by a procedure which comprises:
    1) distilling off solvent to leave a hot molten residue;
    2) washing the residue while molten with water to remove alkali metal chloride by-product and water-soluble impurities, if any, from the 2-bromo-6-methoxynaphthalene residue; and
    3) crystallizing the 2-bromo-6-methoxynaphthalene from a liquid medium.

13. A process according to claim 6 wherein said solvent is at least substantially entirely composed of 2-propanol, and wherein the strong base is formed by mixing sodium hydroxide and/or potassium hydroxide with 2-propanol.

14. A process according to claim 13 wherein recovery and purification of 2-bromo-6-2 methoxynaphthalene is effected by a procedure which comprises:
    1) distilling off solvent to leave a hot molten residue;
    2) washing the residue while molten with water to remove alkali metal chloride by-product and water-soluble impurities, if any, from the residue;
    3) distilling 2-bromo-6-methoxynaphthalene from the washed residue; and
    4) crystallizing the 2-bromo-6-methoxynaphthalene from a liquid medium.

15. A process according to claim 14 wherein said crystallization is conducted in 2-propanol.

16. A process comprising:
    A) reacting 1,6-dibromo-2-naphthol with hydrogen or a precursor compound that generates nascent hydrogen in the medium of the reaction, in a halogen-containing liquid solvent comprising at least 50% by weight of (a) at least one organic halide solvent in which the halogen content has an atomic number of 35 or less, or (b) a mixture of water and at least one such organic halide solvent, and in the presence of catalytically effective amounts of (i) a tungsten carbide-based catalyst, and (ii) at least one phase transfer catalyst, such that 6-bromo-2-naphthol is formed;
    B) separating 6-bromo-2-naphthol from the organic halide solvent so that the 6-bromo-2-naphthol is at least substantially completely free from halogen-containing impurity content; and
    C) methylating at least a portion of the resultant 6-bromo-2-naphthol with methyl bromide or methyl chloride, or both, in a halogen-free liquid solvent comprising at least 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base such that 2-bromo-6-methoxynaphthalene is formed.

17. A process according to claim 16 further comprising recovering and purifying at least a portion of the 2-bromo-6-methoxynaphthalene formed therein.

18. A process according to claim 17 wherein said halogen-containing solvent is ethylene dichloride, and wherein the separation of 6-bromo-2-naphthol from the ethylene dichloride is effected by distilling off most of the ethylene dichloride and then adding water and distilling off the remainder of the ethylene dichloride azeotropically with water.

19. A process according to claim 17 wherein the methylation of 6-bromo-2-naphthol is conducted using methyl chloride.

20. A process according to claim 19 wherein the liquid phase of the reaction between 1,6-dibromo-2-naphthol and hydrogen contains hydrogen bromide during at least substantially the entire reaction period of said reaction.

21. A process according to claim 19 wherein said halogen-containing solvent is ethylene dicliloride, wherein the liquid phase of the reaction between 1,6-dibromo-2-naphthol and hydrogen contains hydrogen bromide during at least substantially the entire reaction period of said reaction, and wherein the separation of 6-bromo-2-naphthol from the ethylene dichloride is effected by distilling off most of the ethylene dichloride and then adding water and distilling off the remainder of the ethylene dichloride azeotropically with water.

22. A process according to claim 19 wherein said halogen-free solvent is water, or at least one alcohol, or a mixture of water and at least one alcohol.

23. A process according to claim 21 wherein said halogen-free solvent is water, or at least one alcohol, or a mixture of water and at least one alcohol.

24. A process according to claim 21 wherein said halogen-free solvent is 2-propanol, or a mixture of 2-propanol and water.

25. A process according to claim 21 wherein said halogen-free solvent is at least 98% by weight of at least one alcohol, and wherein the strong base is formed by mixing at least one alkali metal oxide or hydroxide with at least one alcohol.

26. A process according to claim 25 wherein the alkali metal of said oxide or hydroxide is sodium or potassium, or both, and the recovery and purification of 2-bromo-6-methoxynaphthalene is effected by a procedure which comprises:
 1) distilling off solvent to leave a hot molten residue;
 2) washing the residue while molten with water to remove alkali metal chloride by-product, remains of phase transfer catalyst, and other water-soluble impurities, if any, from the residue;
 3) distilling 2-bromo-6-methoxynaphthalene from the washed residue; and
 4) crystallizing the 2-bromo-6-methoxynaphthalene from a liquid medium.

27. A process according to claim 25 wherein the alkali metal of said oxide or hydroxide is sodium or potassium, or both, and the recovery and purification of 2-bromo-6-methoxynaphthalene is effected by a procedure which comprises:
 1) distilling off solvent to leave a hot molten residue;
 2) washing the residue while molten with water to remove alkali metal chloride by-product, remains of phase transfer catalyst, and other water-soluble impurities, if any, from the 2-bromo-6-metboxynaphthalene residue; and
 3) crystallizing the 2-bromo-6-methoxynaphthalene from a liquid medium.

28. A process according to claim 25 wherein said solvent is at least substantially entirely composed of 2-propanol, and wherein the strong base is formed by mixing sodium hydroxide and/or potassium hydroxide with 2-propanol.

29. A process according to claim 28 wherein recovery and purification of 2-bromo-6-methoxynaphthalene is effected by a procedure which comprises:
 1) distilling off solvent to leave a hot molten residue;
 2) washing the residue while molten with water to remove alkali metal chloride by-product, remains of phase transfer catalyst, and other water-soluble impurities, if any, from the residue;
 3) distilling 2-bromo-6-methoxynaphthalene from the washed residue; and
 4) crystallizing the 2-bromo-6-methoxynaphthalene from a liquid medium.

30. A process according to claim 29 wherein said crystallization is conducted in 2-2 propanol.

31. A process according to claim 1 which further comprises:
 c) converting 2-bromo-6-methoxynaphthalene from b) into a Grignard reagent; and d) reacting Grignard reagent from c) with N,N-dimethyl formamide such that 6-methoxy-2-naphthaldehyde is formed.

32. A process according to claim 31 wherein the methylation in a) is conducted using methyl chloride.

33. A process according to claim 31 further comprising subjecting 6-methoxy-2-naphthaldehyde from d) to base-catalyzed aldol condensation with acetone such that 4-(6'-methoxy-2'-naphthyl)-3-buten-2-one is formed.

34. A process which comprises:
 A) reacting 1,6-dibromo-2-naphthol with hydrogen or a precursor compound that generates nascent hydrogen in the medium of the reaction, in a halogen-containing liquid solvent comprising at least about 50% by weight of (a) at least one liquid organic halide solvent in which the halogen content has an atomic number of 35 or less or (b) a mixture of water and at least one such liquid organic halide solvent, and in the presence of catalytically effective amounts of (i) a tungsten carbide-based catalyst, and (ii) at least one phase transfer catalyst, such that 6-bromo-2-naphthol is formed;
 B) separating 6-bromo-2-naphthol so formed from said organic halide solvent so that the 6-bromo-2-naphthol is at least substantially completely free from any halogen-containing impurity content;
 C) methylating 6-bromo-2-naphthol from B) with methyl bromide or methyl chloride, or both, in a halogen-free liquid solvent comprising at least 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base such that 2-bromo-6-methoxynaphthalelie is formed;
 D) recovering and purifying 2-bromo-6-methoxynaphthalene so formed;
 E) converting 2-bromo-6-methoxynaphthalene from D) into a Grignard reagent; and F) reacting Grignard reagent from E) with N,N-dimethyl formamide such that 6-methoxy-2-naphthaldehyde is formed.

35. A process according to claim 34 wherein said halogen-containing solvent in A) is ethylene dichloride; wherein in B) the separation of 6-bromo-2-naphthol from the ethylene dichloride is effected by distilling off most of the ethylene dichloride and then adding water and distilling off the remainder of the ethylene dichloride azeotropically with water; and wherein the methylation in C) is conducted using methyl chloride.

36. A process according to claim 34 wherein A) is conducted in the presence at the start of the reaction of a small, reaction-initiating amount of hydrobromic acid or hydrogen bromide, and wherein in A) hydrogen bromide is substantially continuously purged from the reaction mixture substantially as soon as it is formed.

37. A process according to claim 34 further comprising subjecting 6-methoxy-2-naphthaldehyde from F) to base-catalyzed aldol condensation with acetone such that 4-(6'-methoxy-2'-naphthyl)-3-buten-2-one is formed.

38. A process comprising reacting 1,6-dibromo-2-naphthol with hydrogen or a precursor compound that generates nascent hydrogen in the medium of the reaction, in a halogen-containing liquid solvent comprising at least 50% by weight of (a) at least one organic halide solvent in which the halogen content has an atomic number of 35 or less, or (b) a mixture of water and at least one such organic halide solvent, and in the presence of catalytically effective amounts of (i) a tungsten carbide-based catalyst, and (ii) at least one phase transfer catalyst, such that 6-bromo-2-naphthol is formed.

39. A process of producing 6-bromo-2-naphthol that comprises reacting 1,6-dibromo-2-naphthol with hydrogen or a precursor compound that generates nascent hydrogen in the medium of the reaction, in a halogen-containing liquid solvent comprising at least about 50% by weight of (a) at least one liquid organic halide solvent in which the halogen content has an atomic number of 35 or less or (b) a solvent mixture consisting essentially of the combination of water and at least one such liquid organic halide solvent, and in the presence of catalytically effective amounts of (i) a tungsten carbide-based catalyst, and (ii) at least one phase transfer catalyst, and in the presence at the start of the reaction of a small, reaction-initiatina amount of an acid or acid anhydride, such that 6-bromo-2-9 naphthol is formed, and substantially continuously purging hydrogen bromide from the reaction mixture substantially as soon as it is formed.

40. A process according to claim 39 wherein the acid or acid anhydride is hydrobromic acid or hydrogen bromide, and wherein the reaction is conducted at temperatures in the range of about 90 to about 120° C. at pressures in the range of about 65 to about 120 psig.

41. A process which comprises:
a) methylating 6-bromo-2-naphthol with methyl bromide or methyl chloride, or both, in a halogen-free liquid solvent comprising at least about 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base such that 2-bromo-6-methoxynaphthalene is formed;
b) recovering and purifying 2-bromo-6-methoxynaphthalene so formed; and
c) contacting 2-bromo-6-methoxynaphthalene from b) with methylvinylketone in the presence of a palladium (II) catalyst at a temperature of from about 50° C. to about 200° C. for a time sufficient to cause reaction such that 4-(6'-methoxy-2'-naphthyl)-3-buten-2-one is formed.

42. A process according to claim 41 wherein the methylation in a) is conducted using methyl chloride.

43. A process according to claim 42 further comprising hydrogenating 4-(6'-methoxy-2'-naphthyl)-3-buten-2-one from c) with hydrogen in the presence of a hydrogenation catalyst such that nabumetone is formed.

* * * * *